United States Patent
Zhou et al.

(10) Patent No.: US 12,031,140 B2
(45) Date of Patent: Jul. 9, 2024

(54) GLYCINE REGULATORY ELEMENTS AND USES THEREOF

(71) Applicant: SYNGENTA CROP PROTECTION AG, Basel (CH)

(72) Inventors: Ailing Zhou, Research Triangle Park, NC (US); Jonathan Cohn, Research Triangle Park, NC (US); Michele Susan Yarnall, Research Triangle Park, NC (US); Yuejin Sun, Research Triangle Park, NC (US); Zhongying Chen, Research Triangle Park, NC (US); Qiudeng Que, Research Triangle Park, NC (US); Lucy Qin, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 1 day.

(21) Appl. No.: 17/772,797

(22) PCT Filed: Nov. 23, 2020

(86) PCT No.: PCT/US2020/061749
§ 371 (c)(1),
(2) Date: Apr. 28, 2022

(87) PCT Pub. No.: WO2021/108290
PCT Pub. Date: Jun. 3, 2021

(65) Prior Publication Data
US 2023/0036103 A1 Feb. 2, 2023

Related U.S. Application Data

(60) Provisional application No. 62/939,762, filed on Nov. 25, 2019.

(51) Int. Cl.
*C12N 15/82* (2006.01)

(52) U.S. Cl.
CPC ..... *C12N 15/8222* (2013.01); *C12N 15/8271* (2013.01)

(58) Field of Classification Search
CPC .............. C12N 15/8222; C12N 15/8271
See application file for complete search history.

(56) References Cited

U.S. PATENT DOCUMENTS

| | | | |
|---|---|---|---|
| 2009/0320160 A1* | 12/2009 | Li | C12N 15/8251 800/290 |
| 2015/0353957 A1 | 12/2015 | Schultheiß et al. | |
| 2016/0194657 A1 | 7/2016 | Bhattacharyya et al. | |

FOREIGN PATENT DOCUMENTS

| | | |
|---|---|---|
| CN | 104152454 A | 11/2014 |
| WO | 2018102816 A1 | 6/2018 |
| WO | 2019027789 A1 | 2/2019 |

OTHER PUBLICATIONS

An, G., Ebert, P.R., Yi, B.Y. et al. Both TATA box and upstream regions are required for the nopaline synthase promoter activity in transformed tobacco cells. Molec Gen Genet 203, 245-250 (1986). https://doi.org/10.1007/BF00333961 (Year: 1986).*
Bianchi, Marzia et al. "A potent enhancer element in the 5'-UTR intron is crucial for transcriptional regulation of the human ubiquitin C gene." Gene vol. 448,1 (2009): 88-101. doi:10.1016/j.gene.2009. 08.013 (Year: 2009).*
Jan-Elo Jørgensen, Jens Stougaard, Anne Marcker, Kjeld A. Marcker, Root nodule specific gene regulation: analysis of the soybean nodulin N23 gene promoter in heterologous symbiotic systems, Nucleic Acids Research, vol. 16, Issue 1, Jan. 11, 1988, pp. 39-50, https://doi.org/10.1093/nar/16.1.39 (Year: 1988).*
De La Torre, Carola M, and John J Finer. "The intron and 5' distal region of the soybean Gmubi promoter contribute to very high levels of gene expression in transiently and stably transformed tissues." Plant cell reports vol. 34,1 (2015): 111-20. doi: 10.1007/s00299-014-1691-7 (Year: 2015).*
Karen M K de Vooght, Richard van Wijk, Wouter W van Solinge, Management of Gene Promoter Mutations in Molecular Diagnostics, Clinical Chemistry, vol. 55, Issue 4, Apr. 1, 2009, pp. 698-708, https://doi.org/10.1373/clinchem.2008.120931 (Year: 2009).*
Cornejo, MJ., Luth, D., Blankenship, K.M. et al. Activity of a maize ubiquitin promoter in transgenic rice. Plant Mol Biol 23, 567-581 (1993). https://doi.org/10.1007/BF00019304 (Year: 1993).*
Zheng, Zhenwei, et al. "5' distal and proximal cis-acting regulator elements are required for developmental control of a rice seed storage protein glutelin gene." The Plant Journal 4.2 (1993): 357-366. (Year: 1993).*
Hernandez-Garcia, C.M., Martinelli, A.P., Bouchard, R.A. et al. A soybean (Glycine max) polyubiquitin promoter gives strong constitutive expression in transgenic soybean. Plant Cell Rep 28, 837-849 (2009). https://doi.org/10.1007/s00299-009-0681-7 (Year: 2009).*
Rodríguez-Leal, Daniel, et al. "Engineering quantitative trait variation for crop improvement by genome editing." Cell 171.2 (2017): 470-480. (Year: 2017).*
International Search Report and Written Opinion for International Application No. PCT/US2020/061749 dated May 4, 2021.

(Continued)

*Primary Examiner* — Charles Logsdon
*Assistant Examiner* — Kelsey L McWilliams
(74) *Attorney, Agent, or Firm* — Dale Skalla

(57) ABSTRACT

Provided herein are regulatory elements, such as promoters and terminators, derived or obtained from various *Glycine* species. Such regulatory elements are useful for expression cassettes for plants, such as soybean. Such expression cassettes generally contain a promoter and terminator sequence to control expression of each coding sequence. Provided are promoters and terminators which are useful for expressing insect resistance and herbicide tolerance genes.

19 Claims, 10 Drawing Sheets

Specification includes a Sequence Listing.

(56) References Cited

OTHER PUBLICATIONS

Zhang Ning et al: "Isolation & characterization of "GmScream" promoters that regulate highly expressing soybean (Glycine maxMerr) genes", Plant Science, Elsevier Ireland Ltd, IE, vol. 241(2), Oct. 21, 2015, pp. 189-198.
Partial Supplementary European Search Report for EP Application No. 20893020.6 dated Dec. 4, 2023.
Hernandez-Garcia Carlos M. et al: "High level transgenic expression of soybean (Glycine max) GmERF & Gmubi gene promoters isolated by a novel promoter analysis pipeline", BMC Plant Bio., Biomed Central, London, GB, vol. 10(1), Nov. 4, 2010, p. 237.

* cited by examiner

SEQUENCE LISTING

<160> NUMBER OF SEQ ID NOS: 31

<210> SEQ ID NO 1
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 1

```
aaaactttca catgaatagc acgaagaatc acaatgaacg attgatcttc ttttaaaatc    60
aaatattaat tgggaaataa aaaaataaaa aatggaagtt cacaatatag tgttcgtgtg   120
cttttcatga aaactgtttt tgtaactttc agcatttttc atataattag gtcatgttgg   180
gtataattag ctataaaatt agttaaaaat ttaaaaatta gttggtaact taaagttaaa   240
aagtaactta ttaaattaaa aatatttaa taaaattaat tgttaaaata attgaaaagt   300
ataaaataac aaaaaataat aaatcaatta atttaaataa gataactagg aaaataaata   360
aaagattaaa aaaactaaa aaactaaaaa actaaagttt taaataatgt ttaaaaatag   420
ttaaaaatta ttaaaaactt atttataaaa cagttaaatt ataaacaaac ttttcgctta   480
tgaaaaataa aagcttacct aactttagta gacaacttgt ccaacaatta gttgatacct   540 attgcccta agttttcttt aatatcaatt attggttttg tcaacaagct atcttttaat   600
cttaatttat tggtaaaaaa tccgtcgcct tcaagttaca tcatttaaca catctgctca   660
ttagaaaaat aaaattcttc ctaaacgatt agtagaaaaa atcatttaa taatgaataa   720 gaaagaaata ttaggaaaaa ataacttcat ttaaaaaaaa catttggatt atattttact   780
ttaaaatatc taaatatttt taatgcacta atttttatata cactgtaact aaaagtatac   840
aagttattat gttatgtatc ataaagaaat acttaaaaaa tctactgaag aatatcttac   900
```

```
aaagtaaaaa taaaataaga aataagttag tggaataatt atgattttat ttgaaaattg       960
aaaaaataat tattaaagaa tttagtggag taagaaagct ttccgattat tcttttttc      1020 cataataaaa aaatctagca tgacagcttt tccatagatt ttaataatgt aaaatactag     1080
tagcagccga ccgttcaggt aatggaccct ataaaatttc gaacgctcca ctccacttgc     1140
aacgagtgcg ggccccaatt taataacgcc gtcgtaacag ataaagtcca acgtgaagcg     1200
gtgaaggtgc atctctgact ccgtcaagat tacgaaaccg ctaattacga aggactcccc     1260
gaaaatgcat ccaataccga aatatcatgt gtgataagca ccaagtgaca ccatacatga     1320
gcacgcgtca caatatgatt ggagaacagt tccaccacat atgctataaa atgcccccac     1380
acccctcgtc catcttcgca gttcaattcc aatcaaatta gttcattctc tttgcgcagt     1440
tccctacctc tccattcaag gttcgtaaat ttttctgtt tttctttttt cttttttcg      1500 ttattgtttg ttcttcatca gcatgatgtt gatttgattg tgttctacat agtttcatcg     1560
aatcttaatt ttcataatca gaatcagctt ttattaatgc aagaactttt ttaatggatg    1620
attttacaat cgtatattag gtctaattag agttttttt cataaaaaat ttcagatccg     1680
tttacaacaa gccttaattt agattctgta gtcgtagatt agggtttttt ttttcattta    1740
ttacttcaga tccgttaaag aacagcctta tttgttgata cttcagtcgt ttttcaagaa    1800
attgtcagac cagttgaaaa aagcctgatt cgttgattct gtatagtttt tcaagagata   1860
ttgctcagat ctgttagcaa ctgccttatc tgttgattct atggccatag attaggggtt    1920
tttttctctc catgaaattg cttcttaaaa ctacgtgatg gattttgatt ctgatttatc    1980
tgtgattgtt gattctacag                                               2000
```

<210> SEQ ID NO 2
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 2

```
tacgaaaaac tttcacatga atagcacgaa gaatcacaat gaacgattga tcttatttta        60
aaaacaaata ttaattggga aataaaaaaa taaaaaatgg aagttcacaa tatagtgttc       120
gtgtgctttt catgaaaact gttttgtaa cttcagcat tttacatata attaggtcat         180
gttgggtata attagctata aaattagtta aaaatttaaa aatttgttag taacttaaag       240
ttaaaaatta acttattaaa ttaaaatat tttaataaaa ttaactgtta aaataattga        300
aaagtataaa ataacaaaaa taataaatca taattaattt aaataagata actaggaaaa      360
taaataaaag attaaaaaaa taaaaaacta agtttttaaa taatgtttat aaaaagttaa     420
aaattattaa aaattattta taaaacagtt aaattataaa caaacttttc gcttatgaaa      480
aataaaagct tacctaactt tagtagacaa cttgtccaac aattagttga tacctattgc      540
ccttaaagta tcaattattg gttttgtcaa caagctatct tttaatctta atttattggt       600
aaaaaatccg tcgccttcaa gttacatcat ttaacacatc tgctcattag aaaaataaaa       660
ttcttcctaa acgattagta gaaaaaatca ttttaataat gaataagaaa gaatatattag     720 ggaaaaataa cttcatttaa aaaacatttt ggattatatt ttaccttaaa atatctaaat      780 attttaaat gactaattt ttatattttt atatacactg taactaaaag tatacaagtt        840
attatgttat gtatcataaa gaaatactta aaaaatctac tgaaaaatat cttacaaagt     900
```

-continued

| | |
|---|---|
| aaaaataaaa taagaaataa gttagtggga taattatgat tttatttgaa aattgaaaaa | 960 |
| ataattatta aagaatttag tggagtaaga aagatttccg attattcttt ttttccataa | 1020 |
| taaaaaaaat ctagcatgac aacttttcca tagatttaa taatgttaaa tactagtagc | 1080 |
| agccgaccgt tcaggtaatg gaccctataa aatttcgaac gctccactcc acttgcaacg | 1140 |
| ggtgcgggcc ccaatttaat aacgccgtcg taacggataa agtccaacgt gaagcggtga | 1200 |
| aggtgcatct ctgactccgt caagattacg aaaccgctaa ttacgaagga ctccccgaaa | 1260 |
| atgataccga aatatcatgt gtcataagca ccaagtgaca ccatacatta gcacgcgtca | 1320 |
| caatatgatt ggagaacagt tccaccacat atgctataaa atgcccccac acccctcgtc | 1380 |
| catcttcgca gttcaattcc aatcaaatta gttcattctc tttgcgcagt tccctacctc | 1440 |
| tccattcaag gttcgtaaat ttttttctgtt tttctgtttt tctttttttc gttattgttt | 1500 |
| gttcttcatc agcatgatgt tgatttgatt gtgttttaca tagtttcatc gaatcttaat | 1560 |
| tttcataatc agaatcagct tttattaatg caagaacgtt tttaatggat gattttacaa | 1620 |
| tcgtatatta ggtctaatta gagttttttt ttcataaaaa atttcagatc cgtttacaac | 1680 |
| aagccttaat ttagattctg tagtagtaga ttggggtttt ttttttttt atgaattact | 1740 |
| tcagatccgt taaagaacag ccttatttgt tgatacttca gtcgttttc aagaaattgt | 1800 |
| tcagaccagt tgaaaaaagc ctgattcgtt gattctgtat agttttcaa gagatattgc | 1860 |
| tcagatctgt tagcaactgc cttatctgtt gattctatgg ccatagatta ggggttttt | 1920 |
| tttttctctc catgaaattg cttcttaaaa ctacgagatg gattttgatt ctgatttatc | 1980 |
| tgtgattgtt gattctacag | 2000 |

```
<210> SEQ ID NO 3
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 3
```

| | |
|---|---|
| aattaccctc gttgtcatac ctatttaga gccaatgcat aatgatatgg acacttgttt | 60 |
| atcaaggagt taattatttt ttcttttgtt tttcacttga aaaaagatt gccatttgaa | 120 |
| ataggataac caattcttgt atttttgtat ttgacttata taactaaaaa aacaaaaatt | 180 |
| actcaaataa ttcaagtata aaattattta tataatgat taaaaacatt gtttggggt | 240 |
| gagaaattga tttaattaaa aaagagatta agttaacatg aaatagaatt aaattaaaaa | 300 |
| ctttatttta aataaaataa tgtttaaaaa tagaattaaa taagataact aagaaaataa | 360 |
| ataaaaatta aaaactaaaa aactaaagtt ttaaaaaaat ttatttaaa taatgtttaa | 420 |
| aagggttaaa aattatttaa aaacttattt ataaaatagt taaataaact tttcactaat | 480 |
| aaaaaataaa agcttaccta acctagtag acaacttgtc caacaattag atgatgccca | 540 |
| ttgccctta agttttcttt aacatcaatt attgttttg tcaacaagct atctttggt | 600 |
| cttatttat tggtgaaaaa tccgtcgcct tcaagttgcg tcggttaaca catctcctca | 660 |
| ttagaaaaat aaaattcttc cctaaacgat tagtagaaaa aatcatttaa taataaataa | 720 |
| gaaagaaaaa ttaggaaaaa aataacttca tcttaaaaaa tatttagatt atattttact | 780 |
| ttaaaatatc taaatttttt aaatgactaa ttttatatac actgtaacta gaaaatataca | 840 |
| agttattatc ttatatgtct cataaagaaa tacttaaaaa atctagtgaa gaatatctta | 900 |
| caaagtaaaa aataaataag aaagaattta gtgggataat tatgatttta tttgaaaatt | 960 |

```
gaaaaataat tattaaagaa tttagtggag taagaaagct ttccgattat tcttttcttg       1020
tccataataa aaaaatctag catgacggct tttccataga ttttaataat gtaaaatact       1080
attagcagct gaccgttcag gtcatggaga cagtggggtc ctataaaact tagaacgctc       1140
cacatgcaac gggtgcgggc taaaattgtg acgtgggacc caatttagtt acgccgtcgt       1200
aacagataaa accaagtgtg aagcggtgaa ggtgcatctc tgactccgtc aaaattacga       1260
aaccgctaac tacgaagggc tcacccgaaa ttaggaaaat gcatccaata ccgaaatatc       1320
atgtgtgtca taagcaccaa gtgacaccat acatgcccac gcgtcacaat atgagtggag       1380
aacgattcca ccacatatgc tataaaatgc cccacaccct tcgtccttct tcgcagttca       1440
attccaatca aattagttca ttctctttc gcatttccct acctaccct tcaaggttcg        1500 tcgattttt ttttctttat tgtttgttct tcatcagcat gatgttgatt tgattgtgtt       1560
ttacatagtt tcatcgattc ttaattttca taatcagatt cagcttttat tattgcaaga       1620
acgtccttaa ttgatgattt tataatcgca aattaggtct aattagagtt ttttcattaa       1680
aaaattcaga tccgtttaca acaaccttaa tcgttgattc tgtagtcgta gattagggtt       1740
ttttcatgaa ctacttcaga tccgttaaac aacaccccta tttgttgata cttcagtcga       1800
tttttcaaga aattgttcag atccgttgat caaagccttt cgttggttct gtatagtttt       1860
ttaagagata ttgctcagat ccgttagcaa ctgcttatt tgttgatttt atggccatag        1920
attagttgtt ttcttcttca tgaaactgct taaaattgtg atggattttg attctgattt       1980
atctgtgatt gaccttacag                                                  2000

<210> SEQ ID NO 4
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 4 attcatttt aatatgactt attgtcctaa aaaatttatt ttcgtaaatt aaataaaatg         60 aatttttct ttctttcaaa taatctaact agtcataatg agaatttgct aaaaaaaata        120
cataatgaga atcaatatta aatttattta tcaatataaa ttaatatcat tttatagaaa       180
aaataaaatt ttaaaattaa tcatatagaa ataaattttt tatattattg gttcaaatta       240
aaataatgtt aaaaaataaa atagattatt aattgatatt gatataaaat ttaaataaat       300
aatataatga ttgttttta ttttattaat atgtaatcaa ctaattatta ttttttgaat        360
caattagtac ttaaagataa tattaattga tttttttatc cttttaggtg gcatgtgtgc       420
tgtgagacat tatcatcaat ttaatatgat atgatacata gatatagata taaatataga       480
tatataaata tgtagattgg aatgatataa tatattttaa atataaatta tatatatata       540
tatatatttg taatatattt tttcacatat atatttaaa aactataagt attttttcat        600
gagacaatta ttgtcgaatt gaataggttc attacttgtg agactcaatg agatttatat       660
ttgtaattaa attttaaatt tgtgaaatta aaatgataaa aaatacatta aaaatcataa       720
taatataaaa aacttatatt tataatattg tgacagtaaa aaatctcttc ccattatact       780
taaaaataaa aaattaaata aataggccgc gccctagggt ttttgagaaa aaatctcttc       840
ccacgcattc aactgcactg tacgtcgtcg ttttcacagc cgcataatag aagccgcgtt       900 ccccaacct tcctcacaac attatcggac cctcccgcac cgtcaccaaa ataaatatcc        960
```

| | |
|---|---|
| acgcgctatt aggcgcgtga aactcactct aatccgaaac cacgagacgt gagaagcacg | 1020 |
| agcttttagc gagcgtttca attgtcgcta cgaaagcaga gaaagataca aactgaacta | 1080 |
| gggtaaatta gtaagggtat tttcgtaaac agaagaaaag agttgtagct ataaataaac | 1140 |
| cctctaaccc tcgtcgcatt acttctcttc acacctttgt tcactcttct tctcttgcgg | 1200 |
| ctagggtttt agcgcagctt cttcttggtt cgtattcttc caccgtttta tggattttat | 1260 |
| tccttcgatt catgtttatt ctattggttt atgttgcttg caatttatat tttctgaatc | 1320 |
| tattgttgtt gttttcaatt ttatccatgt ttcatagatc aattttgtgt gtagtatgtg | 1380 |
| cttttcttc ttcttttcg ttcgagttgt tgttaataac ggtgctaatt gtgttttcaa | 1440 |
| aagtgttttt tatttattta tttttgattt gatgtttttc attttggttt tgggctttta | 1500 |
| tgtgcttgtt atattcaaat ctttggatcc agatcttgta aaagttttg gtttaagaaa | 1560 |
| gttttttggct actgttgaat agatctatta actgttactt taatcgattc aagctaaagt | 1620 |
| ttttggtta ctgatgaata gatctattaa ctgttacttt taatcgattc aagctcaagt | 1680 |
| ttttggtta ctgatgaata gatctatata cgtcacagtg tgctaaacat gcgttatgta | 1740 |
| tgggtgtgcc acaaatttta ctgtctattt atttatcttg tggaatcata ttgtgtttga | 1800 |
| tgcgttatga ttgagcatac ctattttttca gcttgttgga tgatgtgtat ctagataatc | 1860 |
| tgatatttt acggtctga aaggttttgt aaatggcaga ggccttaatg ttgttgaact | 1920 |
| tattttttta tttatgtggt gtgttgaact atgatggttt tgacaacttt ttctctggat | 1980 |
| tttttgcaga tttaaggaag | 2000 |

<210> SEQ ID NO 5
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 5

| | |
|---|---|
| agtttttttc tttcaaagaa tctaaatggt cataatgaga attctctaaa aaaatacata | 60 |
| atgagaataa ttatggaatt tatttattaa taaaaattaa tagcattttg atagacaatt | 120 |
| aataaaattt taaaaataac catatagaaa taataatttt tttactatcg gttccaatta | 180 |
| aaataatgat aaaaaataaa atagattatt aattgatatt gatatgaaat ttaaataaag | 240 |
| aatataatca tatattttat tgatatatga tatgatatag attaattgat attgattttg | 300 |
| atatggaatt taaaaataat ataataattg ttttttattta ttaatacgtg taatcaaata | 360 |
| attctcactt tttgaatcaa tcagtgtact taaagataat atcagttgaa tatttttat | 420 |
| ccttttacgt gtgctgtgag acattatcat caattgtgtt gtatatgata tatagatata | 480 |
| gatatataaa tatatagatt gagtgatata atatatttaa aatataaatt atatatatgt | 540 |
| tttaatatat ttttgcatat atatatat ttgtaaaaac tagaagtatt ttttcatgag | 600 |
| ataattatta tcgagttgaa taagtctatt atttgtgaga gccaaccata tttatatatg | 660 |
| tgattaaatt ttatctttgt gaaattaaaa ataataaaaa taccttaaaa atcataataa | 720 |
| tagaaaaact tatattata atttaccatt atacttaaaa aaaattaaat aaatattata | 780 |
| aatataaata ctatcgagta atggccgcgc tagggttttt gagaaaaaat cttcccacgc | 840 |
| actcaactgc actgtacggc gtcgttttca cagccgcata atagaagccg cgttccccaa | 900 |
| cccttcctca caacattctc ggaccctcca gcaccgtcac ccaaacaaat atccacgcgg | 960 |
| tagtaggcgc gtgaaacaaa ctctaatccg aactacgaga cgtgagaagc acgcgcttta | 1020 |

```
gcgagcgttt caattgtcgc tacgaaagca gagaaggata caaacggaac tagggtaaat    1080
tagtaagggt aatttcgtaa acagaagaaa agagttgtag ctataaataa accctctaac    1140
cctcgtcgca ttacttctct tcacaccttt gttcactctt cttctcttgc ggctagggtt    1200
ttagcgcagc ttcttctagg ttcgttatct accaccgttc tatggatttt attccttcta    1260
ttcgtgttta ttctattggt ttatgttgct tgcaatatgt ttttctgaa tctgtcgtcg     1320 ttgtcttcaa ttttatccat gtttcagaga tcaattttgt ttgtgtagta tgtgcttatt    1380
cttcttcttt tcgttcgagt tgttaataac ggtgctatgg tgttttcaaa agtgtttttt    1440
ttattacttt tgatttaaag ttttttttggt aaggctttta tttgcttgtt atattcaaat   1500
ctttggatcc agatcttata taagtttttg gttcaagaaa gttttttggtt actgatgaat   1560 agatctatta actgttactt taatcgattc aagctaaagt ttttggtta ctgatgaata     1620 gatctattat ctgttacttt taatcggttc aagctcaagt ttttggtta ctgatgaata     1680 gatctatata cgtcacagtg tgctaaacat gcccttgttt tatctcgatc ttatgtatgg    1740
gagtgccata aattttgtta tgtctatttt tttatctgtt ggaatcatac tgagtttgat    1800
gcgttacgat tgagcatacc tatttttggg cttgttgtat ggtgggtatt tagatcttaa    1860 tcttttatg cttatgaaag gttttgtaat gacaaaggtc ttaatgttgt taaactttta    1920
ttttactttt atatggtgtg ttgatgtgtt atggttttga caactttttt tttttctgga    1980
tttttgcaga tttaaggaag                                                2000

<210> SEQ ID NO 6
<211> LENGTH: 2000
<212> TYPE: DNA
<213> ORGANISM: Artificial sequence
<220> FEATURE:
<223> OTHER INFORMATION: Synthetic polynucleotide

<400> SEQUENCE: 6
attcattttt aatatgactt attgtcctaa aaaatttatt ttcgtaaatt aaataaaatg      60
aattttttct ttctttcaaa taatctaact agtcataatg agaatttgct aaaaaaaata    120
cataatgaga atcaatatta aatttattta tcaatataaa ttaatatcat tttatagaaa    180
aaataaaatt ttaaaattaa tcatatagaa ataatatttt tatattattg gttcaaatta    240
aaataatgtt aaaaaataaa atagattatt aattgatatt gatataaaat ttaaataaat    300
aatataatga ttgttttttta ttttattaat atgtaatcaa ctaattatta tttttttgaat   360 caattagtac ttaaagataa tattaattga ttttttttatc cttttaggtg gcatgtgtgc    420
tgtgagacat tatcatcaat ttaatatgat atgatacata gatatagata taaatataga    480
tatataaata tgtagattgg aatgatataa tatattttaa ataaaatta tatatatata    540 tatatatttg taatatattt tttcacatat atattttaaa aactataagt attttttcat    600
gagacaatta ttgtcgaatt gaataggttc attacttgtg agactcaatg agatttatat    660
ttgtaattaa atttttaaatt tgtgaaatta aaatgataaa aaatacatta aaaatcataa    720
taatataaaa aacttatatt tataatattg tgacagtaaa aaatctcttc ccattatact    780
taaaaataaa aaattaaata aataggccgc gccctagggt ttttgagaaa aaatctcttc    840
ccacgcattc aactgcactg tacgtcgtcg ttttcacagc cgcataatag aagccgcgtt    900 ccccaacccct tcctcacaac attatcggac cctcccgcac cgtcaccaaa ataaatatcc    960
acgcgctatt aggcgcgtga aactcactct aatccgaaac cacgagacgt gagaagcacg   1020
```

```
agcttttagc gagcgtttca attgtcgcta cgaaagcaga gaaagataca aactgaacta    1080
gggtaaatta gtaagggtat tttcgtaaac agaagaaaag agttgtagct ataaataaac    1140
cctctaaccc tcgtcgcatt acttctcttc acacctttgt tcactcttct tctcttgcgg    1200
ctagggtttt agcgcagctt cttcttggtt cgtattcttc caccgtttta tggattttat    1260
tccttcgatt catgtttatt ctattggttt atgttgcttg caatttatat tttctgaatc    1320
tattgttgtt gttttcaatt ttatccatgt ttcatagatc aattttgtgt gtagtatgtg    1380 cttttctct ttctttttcg ttcgagttgt tgttaataac ggtgctaatt gtgttttcaa    1440
aagtgttttt tatttattta tttttgattt gatgttttc attttggttt tgggcttta    1500 tgtgcttgtt atattcaaat ctttggatcc agatcttgta aaagttttg gtttaagaaa     1560 gttttggct actgttgaat agatctatta actgttactt taatcgattc aagctaaagt     1620
tttttggtta ctgatgaata gatctattaa ctgttacttt taatcgattc aagctcaagt    1680
tttttggtta ctgatgaata gatctatata cgtcacagtg tgctaaacat gcgttatgta    1740
tgggtgtgcc acaaatttta ctgtctattt atttatcttg tggaatcata ttgtgtttga    1800
tgcgttatga ttgagcatac ctattttca gcttgttgga tgatgtgtat ctagataatc    1860
tgatattttt acggttctga aaggttttgt aaatggcaga ggccttaatg ttgttgaact    1920
tattttttta tttatgtggt gtgttgaact atgatggttt tgacaacttt ttctctggat    1980 ttttttgcaga tttaaggaag                                                2000

<210> SEQ ID NO 7
<211> LENGTH: 1614
<212> TYPE: DNA
<213> ORGANISM: Artificial sequence
<220> FEATURE:
<223> OTHER INFORMATION: Synthetic polynucleotide

<400> SEQUENCE: 7
tccaccctca caaaaaaggt tattgcctaa ttaatagtag ggattgaaga agtatcaata      60
atcaataaga gggacatttg gattgacaca aactattagt ataaaaaaaa aatgtaaaac     120
taaatggaca caatctaag aaagcgagta tgtgttgtac tcggaaaaca taacataatg      180
tgattttgat tgtggaaact gaaaacaata acaattaagt tttatttatc tctttgccta     240
acaatttttt taattacttt ttttatagtt tttatgatga agataattaa tattttttac    300
aaatattata ttttcctttt taccatcttt gaagataatt gcttttttt ccaatttaga     360 caaatatttg agtatcaatg atattccttt ttaatccatt attgcaattt aaaagaccat    420
caatgattac attttcaatc aaatgacttt attagtcttc actttacatc gatttaaatc    480
aaactaataa ttttgtatgg actaaatctc tgaacatttt tatatttaca acatatttta    540
acatttatta aataattagt atttaatact attagtagaa taatgggagt agcaggaggg    600
aggcactgag agaatagaga tggcatggaa gtaagcaatc aagtcaaaat cagagttggc    660
caaccccaaa ggctgtagta ggtaagcatg gcccatttta gtttttacat tcatctctca    720
ttttcacctc aacggttcag attcaatctg actccccgat ctcagccgtg gattcaaatg    780
ccacctcagg cacatgcaat tccaaatgga tgaacctaac ccacaatcta atcttgttac    840
ttaggggctt ttccgtcatt aaatgacacc acctaccccc ttctccctat aaatggcaac    900
tcaatccccc ccttagaact cgcagcgctt gatttgaggc caggcaagcc ccactcaacc    960
accacacctc tcctcgttca cgctacccct ttctgctctt cttctacctt tcaaggtact   1020
cttcttcccc tctgttgctg caaccttctc tttctttaag attgcctcaa tttcggatct   1080
```

```
tgcacctctg ggttgctttg cttttgctttt tcctctactg ggttgatttc tgtttcccta   1140
aaccggttta gacgaatgtg aacactactt cttttgttta attactctgg aatacgtgtt   1200
aggctttcag atctagttga aatcgtattg cacttttagg gggagtttgg atttctaata   1260
agaaattgac cttttgctga gaattggttc ggtgattaga gggtttccgt aaattttga   1320 agttttacat gcttgtatct gtttattttt gtttctcaca tctattattg ttaggtgaag   1380
gaaattatgt attgagagtc tgtctgatac taaatataaa cacctcaata ggggctctaa   1440
cactgatttt atcatttgct gcttgtgtgt atggttaaag aaaggcaatt gtgttttaat   1500
tttctgcaag ctttcgtttg ctgaattta tgcatatatt ttcctccctt ttgtgaactt   1560
cctttttgta gttctaattc cattttggt gtctgcagtt ttaaaagtat aaag         1614
```

<210> SEQ ID NO 8
<211> LENGTH: 1001
<212> TYPE: DNA
<213> ORGANISM: Artificial sequence
<220> FEATURE:
<223> OTHER INFORMATION: Synthetic polynucleotide

<400> SEQUENCE: 8

```
aatcgtgcgg gctggttcat caggggatgt tggttacaat aaatgttggt ttcttttctg     60
tactcttgtg tcttcttttc taggtagctt gttttttcgga caaagtttga agtctccacc    120
atcatctcgc aactgttgtt cccagaactg ggttcttgat cgacggtggc aaaattgctt    180
ttatttatct gtgttttaat gtgttgtgtt tgtcggaacc cctgattaca ttttttgttaa   240 gcgcagcgag tttcaggact ttgctgcgtt tgttgctttt ggtttattaa atgtcaactt    300
tctatttgta gtgttcaatt tttggcttgg tttgcttttt ctttataatt tgtgttcaaa    360
ttttggcttg gtttgctttt actataattt gtgttcaaat tttgggttgg atttttttaac   420 gatcggctgt ttgctcttct tcctctgttt tgatgtgttc gtgactatgc aagaatcttc    480
aattttgcta aaataaactt gctttgacaa catagaatca aatccgagtg ctttaatatt    540
cggtggtttg ttttttatttt tggttttatg aaagttaaaa ttttaaaagt aaatcgataa    600
ggtataattg tggttttttat ttatcgagaa ttttttaagt gaatcgatat aatttatttc    660
ccctaaaata aaataccaaa gaatcgaatt cgaactttgt ctttaataaa actactaatt    720
taatcattat ttgttctgtg taagcatgag aaataaattc tacttatctt ttagtttaaa    780
accaaaacag gttaagaata attttttctaa ggccgttatc aaggtcacca aaaatctatt    840
cgatctgacc atatattttc gatacttgta cgattcgcag atgttgattg gaaattgcaa    900
tgaataaatt acaaatgcca aatccgatta tgcaatgaat gaattacaag tgcatttatc    960
cgttttgaat ctgttcatgt ctaccaatgg gagagatttt t                       1001
```

<210> SEQ ID NO 9
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 9

```
gctggagctg atttctgtgt gatgttggat gttcccaaac attttaagaa ctgtaatgtg      60
taatgggtct gtaatgacct ttgaaaataa gtttggtttg tgttgaactc tattgtcgca    120
ttaatgttac tactgtttgt tatcaatgtg tggaactgat atataattat caactctatg    180
```

```
ttggcctatt gtgttgaatt tgttctcaa tccaatgaat tggcgtatat tagtgggttt      240
tttattcttc atgcttgtca cagatgaaaa acagggatga gttgtaagga tggtgaatca      300
tcccacgaat tagattttgg tattataatt taaagatatt attaggtagg aagaactctt      360
ggattagatt ctaaagtgat attatgaaaa cgcactaaag gattttgaac aaactgagat      420
catgatccct agtttcaatt aacttcccct tacctagatt ttatacatat gtaagctaga      480
gtgggaacat tattcagaat cggatccgtt aacagataa aaacaaaagc gatcgggtta       540
atcccatttt tacaaataac aacgcgggtt tatacatgaa acaaatgtca ttaccaagtg      600
atatttttct gctctatact ctatacccgt tttattatca ttaattttgt aattatatgg      660
attaatgaaa ggttcctccc agagtgaaat tgttgtgttg gcgtgcgtgt agagcttctc      720
ttccaacaag agacaagctt gagatcgtgg agtaacctgt cccttaacgt gctctttgtt      780
atacatttca cgtgtttgca gtttgcccgg ggatcatgga atgctggcag aagttggggt      840
tgagtagcaa agttgataat ttaattatgc aggtgcagtc ttttgctgaa ttattcttca      900
aactcatgct ttctattgaa tcttatcaaa caatgtagag tagctatgac tctgtggaga      960
gtgcttggag atgtcacaat gatgctgttt ggaagggact                            1000

<210> SEQ ID NO 10
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 10
atcgtgcggg ctggttcatc aggggatgtt ggttacaata aatgttggtt tattttctat       60
agtctcgtgt cttcttttct aggtagcttg tttttcggac aaagtttgaa gtctccacca      120
tcatctcgca actgttgttc tcagaactgg gttcttgatc gacggtggca agattgcttt      180
tattaatctg tgtttaatg tgtttgtgtt tgtgagaacc cctgattaca ttttattaa        240 gcgcagcgag ttttaggact ttgctgcgtt gttgctttgc ttttataaat gtcaacttc      300 tatttgtgtt caattttggc ttggattgc ttttacttt ataatttgtg ttcaaatttt        360
ggcttggatt ttttaactat cggctgttgc ttttcttctt atgttttgat gtgttcgtga      420
ctatgcaaga atcttcaatt tgctaaaat aaacgtgctt tgacaacata gaatgaaatt       480
cgagtgcaca attcggtata attgagaaat tataattgtg gttttattt attttgagtt      540 ttttaattga acatttccac taaaataaaa tgccgcctaa gaattgaatt tgaacttttg      600
tttttaataa aactactaat ttagtcataa tttcttctgt gtaaccatga gaaataaatt      660
atactgatct tttagtgaaa aaccaacaag gctaagaatg atttttctaa agcctttaga      720
ttagaggcca ctaaaatcta tacgatctgc ccatatattt tcgatacttg aacgattgca      780
gatgttgatt agaagttgca atgaataaat tataagtgcc caatccgatt ttcaccaaaa      840
tctatacgat ctgcccacat atttttcgata cttgaacgat gcagatgtt gattagaaat      900 tgcaatgaat aaattacaag tgccaaatcc gatttttgcaa tgaatgaatt acaagtgcat     960
ttatccgttt taaatctatc catgtctacc aatgggacca                            1000

<210> SEQ ID NO 11
<211> LENGTH: 1001
<212> TYPE: DNA
<213> ORGANISM: Artificial sequence
<220> FEATURE:
<223> OTHER INFORMATION: Synthetic polynucleotide
```

<400> SEQUENCE: 11

```
attcaatcaa accgttcatg cttaatcaag ttgggaacaa caaaaaaaat caaaacaatg        60
tttctgggtt tcggtttcat ttcatcaaga tgatctgttt atcttttttt ttttaatttt       120
aatttaaagt ctttgtattt tgtatgtaaa gatgtaaaat tatgattatt aggtggtgca       180
tgtgttgcgt catgggccaa tgttatcctc tgcttttaag ttggaagagg cccagctcac       240
gtgtgatgta cggctgtgat tgtgtaattt gcaaaatcaa aataacccc cgagtcatat        300 atgcatcttt ttattttatt ttattttatc ttattattga catatttaga caccttttaa       360
aattatgatg atcatctcta aagcaaggta tgaccataat ttttccaaat tgcttttat        420 aactgatttt ggttcatctc ttagaattga ttttggttca gattccaaac atcctttata       480
ttgctactat tttattttc ttttgacccc ccctatgtct tctctctaat atttgtcctc        540
ttccccgaag catatgccaa ggttgggttt ctttatccac gcctgtgccc gttatcactt       600
gctatggata attgaaatcc gtggacagtg aggagtgggg ttggtttaag gtgggtgggt       660
ggatgatgtc tattgcttaa atatgggacc acttttcttc ctcaataatg catatattct       720
agtgttgtcc atttaataat gattcgtgat catagccttg ggaaaaaaat gtacactatt       780
ttttatattt tatgccaaaa tttggacaag cttgatctta tcagcttcag cggggaatgc       840
cacttccttc tagttacttc catggaatcc ttcgcggaaa agacgtggca cttgtgagat       900
gagtaactga aagaaagca ttagtaattt gacacgtata aatcgttgac tcattcttgt        960
gatttagcat ttgcctatta tttttatcaa atgccaacta g                          1001
```

<210> SEQ ID NO 12
<211> LENGTH: 600
<212> TYPE: DNA
<213> ORGANISM: Artificial sequence
<220> FEATURE:
<223> OTHER INFORMATION: Synthetic polynucleotide

<400> SEQUENCE: 12

```
ttcaatcaaa cggttcatga gtaatcaagt tgggacaaca acaaaaaaaa tcaagccaat        60
gtttgtgggt tttggtttca tttcattaag atgatctgtt tatctcttct tttttttttc      120
tttttttaaa tttaaagtct tgtgattttt gtatgtaaag atgtaaaatt atgattatta      180
ggtggtgcat gtgttgcgtc atgggccaat gttatcctct gcttttaagt tggaagaggc      240
ccagcttatg tgtaatgtac ggctgtgatt gtgtaattta atttgcaaaa tcaaaaataa      300
caccagaggc atctctttat tttctctgga ccccaccatg tcttctatgt aatatttgtt      360
gtcctcttcc ccgaagtata tgccaaggtt gggtttcttt atccacgcct gtgcccgtta      420
tcacttgcta tggataattg aaatccggtg agagttagga gtggggttgc gtgggtgggt      480
gggtgggtga tgtctcttgc ttaatatggg accactttc ttcgtcaata atgcacatat        540
tctagggttg tccatttaat aatgatttgt gatcatagcc ttggggaaaa accgtacact      600
```

<210> SEQ ID NO 13
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 13

```
ttcaatcaaa cggttcatgc ttaatcaagt tgggacaac aaaaaatcaa aacaaagttt         60
```

```
gtgggtttcg gtttcatttc atcaagatga tctgtttatc tttttttttt tttttaattt      120
aaagtctttg tattttgtat ttaaagatgt aaaattatga ttattaggtg gtgcatgtgt      180
cgcgtcatgg gccaatgtta tcctctgctt ttaagttgga agaggcccag ctcatctgtg      240
atgtacggct gtgattgtgt aatttgcaaa atcaaaaata accccgagt catatatgct       300 tcttttatt ttatcttatt attaacatat ttagataccct tttaaaatta tgataattat      360
ctctaaaaca aggtctgacc ataatttttc caaattgctt tacattttt agtgattta        420 tagctgattt tggttcatct cttagaattg atttcggttc agctcacggt ctttccaaac      480
atactatata ttgctactac tttatttttct ctagaccccc ctatgtcttc tctctaatat    540
ttgtcctctt ccccgaagta tatgccaagg ttgggtttct ttatccactc ctgtgcccgt     600
tattactttg ctatggataa ttgaaatcag gggagagtga ggagtggggt tggtttaagg     660
tgggtgagtg ggtggatgat gtctattgct taaatatggg accacttttc ttcctcaata    720
atgcacgtat tctagtgttg tccatttaat aatgattcgt gatcatagcc ttgggaaaaa     780
aacgtacaat attttttata ttttgtgcta aaatttggac aagcttgatc ttatcagctt    840
cggcggggaa tgcctcttcc ttctagttac ttccatggaa tccttcacgg aaaagacgtg     900
gcacttgtgg gatgggtaac tgagtagaaa tcatcagtaa ttttgacacg tataaattgt    960
tgactcaatc ttgtgattta gcatttgctt tttattttta                           1000
```

```
<210> SEQ ID NO 14
<211> LENGTH: 999
<212> TYPE: DNA
<213> ORGANISM: Artificial sequence
<220> FEATURE:
<223> OTHER INFORMATION: Synthetic polynucleotide

<400> SEQUENCE: 14
gctggagctg atttctgtgt gatgttggat gttcccaaac attttaggaa ctgtaatgtg       60
taatgggtct gtaatgacct ttgaaaataa gtttggtttg tgttgaactc tattgtccca      120
tcaatgttac tactgcttgt tatcaatgtg tggaattgat atataattat caactctatg      180
ttggcctgtg gtgttgaatt tgttctcaa tccagtgaat tggcgatccg tttaacagat      240
aaaaacaaaa gcgatcgggt taatcccatt tttacagata caacgcagg tttatacatg      300 aaacaaatgt cattaccaat tgatattttt ctgctctata ctctataccc ttttttattat    360 cattaatttt gtaattatat ggattaataa aaggttcctc ccagagttaa attgttgtgc     420
gagggtggca ttgaaaatac atttcacgtg tttgcagttt accgaggatc atggaatgct     480
agcagaagtt ggggttgagt agcaaagttg ataatttaat tatatgcagg tgcagtcttt     540
tgctgaattc ttcttcaaac tcatgctttc tattgaattt tatcaacaat gtggagtgct     600
atgacctgtg gagagtgctt ggagatgtca caatgatgct gtttgggaag ggactatcac    660
ggattccgcc atcgtgatca acagagtgga catgttttat caaaattggg ttcgtgcaca    720
acaatcaaat aaatttagac aggttgcaga attaatggag gtgaatgatt cttggagtcc    780
gtcgactttg gaaggttaaa atgtaacctt gatgcatctc tcaaccatgt tcaaaactgc    840
acagcttttg gttatgcgt tcgggcatct tattgttgcc agaactgatg ttgtgaaacc     900
atgcatgcct gttatggagg gtgaggcgtt aggggttgcag ttggcgattc agtttgttct    960
atatgcggga atgcaaaatg tggactttga aacagattg                            999
```

```
<210> SEQ ID NO 15
<211> LENGTH: 1000
```

<212> TYPE: DNA
<213> ORGANISM: Artificial sequence
<220> FEATURE:
<223> OTHER INFORMATION: Synthetic polynucleotide

<400> SEQUENCE: 15

| | | | | | |
|---|---|---|---|---|---|
| atcgtgcggg | ctggttcatc | agggatgtt | ggttacaata | aatgttggtt | tattttctat | 60 |
| agtcttgtgt | cttcttttct | aggtagcttg | tttttcggac | aaagtttgaa | gtctccacca | 120 |
| tcatctcgca | actgttgttc | tcagaactgg | gttcttgatc | gacggtggca | agattgcttt | 180 |
| tattaatctg | tgttttaatg | tgtttgtgtt | tgtgagaacc | cctgattaca | tttttattaa | 240 |
| acgcagcgag | ttttaggact | tgctgcgtt | gttgctttgc | ttttttaaat | gtcaactttc | 300 |
| tatttgtgtt | caattttggc | ttggatttgc | ttttacttta | taatttgtgt | tcaaatttg | 360 |
| gcttggattt | tttaactatc | ggctgttgct | tttcttccta | tgttttgatg | tgttcgtgac | 420 |
| tatgcaagaa | tcttcaattt | tgctaaagta | aacgtgcttg | gacaacatag | aatgatattc | 480 |
| gagtgcacaa | ttcgttataa | ttgagaagtt | ataattgtgg | tttttattta | ttttgtgagt | 540 |
| tttttaattg | aacatttcca | ctaaaataaa | atgccgtcta | agaattgaat | tctaactttt | 600 |
| gttttaataa | aactactaat | ttagtcataa | tttcttctgt | gtaagcatga | gaaataaatt | 660 |
| atactgatct | tttagggata | aaccaacaag | gctaagaatg | agttttctaa | ggcctgtaga | 720 |
| ggccaccaaa | atctatacga | tctgcccata | tattttcgat | agttgaacta | ttccagatat | 780 |
| tgattggaaa | ttgcaatgaa | taaattacaa | gtgcctaatc | cgattttgca | atgaatgaat | 840 |
| tacaagtgca | tttatccgtt | ttaaatcaat | ccatgtctac | caatgggacc | agtaaaagcc | 900 |
| caagcagata | tcatagtgca | tggtgcatac | accaaacggt | ttatagccag | tcccgaagct | 960 |
| caggctttta | catatatcgt | tgcagcctat | tgttagaaga | | | 1000 |

<210> SEQ ID NO 16
<211> LENGTH: 999
<212> TYPE: DNA
<213> ORGANISM: Artificial sequence
<220> FEATURE:
<223> OTHER INFORMATION: Synthetic polynucleotide

<400> SEQUENCE: 16

| | | | | | |
|---|---|---|---|---|---|
| gctggagctg | atttctgtgt | gatgttggat | gttcccaaac | attttgagaa | ctgtaatgtc | 60 |
| taatgggtct | gtaatgacct | tgaaaataa | gtttggtttg | tgttgaactc | tattgtccca | 120 |
| tcaatgttac | tactgtttgt | tatcactgtg | tggaattgat | atataattat | caactctatg | 180 |
| ttggcatgtt | gtgttgaatt | tgttctcaa | tccagtgaat | tggcgtatat | tagtgggttt | 240 |
| tttattcttc | atgtttgtca | cggaggaaaa | acagggatga | gttgtaagga | tggtgatcat | 300 |
| tccacgaatt | agattttggt | atggtaggtt | aaagatatta | ttaggtaggg | agaacttttg | 360 |
| gattagattc | taaagtgata | ttatgtaaac | gcactaaagg | attttgaaca | aacagatcat | 420 |
| gaccccctagt | ttcaattagc | tgcccattac | ctagatttta | tacatatgta | tgctagagtt | 480 |
| ggaacattag | tcagaatcgg | atccgtttaa | cagataaaaa | caaaagcgat | cgggttaatc | 540 |
| ccatttttac | agataacaac | gcaggttat | acatgaaaca | aatgtcatta | ccaattgata | 600 |
| tttttctgct | ctatactcta | tacccttttt | attatcatta | attttgtaat | tatatggatt | 660 |
| aataaaaggt | tcctcccaga | gttaaattgt | tgtgttgggg | tgcgtgtaga | gcttgagatc | 720 |
| gtggtacctg | tcccttaacg | tgctctttgt | gcgagggtgg | cattgaaaat | acatttcacg | 780 |
| tgtttgcagt | ttaccgagga | tcatggaatg | ctggcggaag | ttggggttga | gtagcaaagt | 840 |

| tgataattta attatgcagg tgcagtcttt tgctgaattc ttcttcaaac tcatgcattc | 900 |
| tattgaattt tatcaacaat gtagagtagc tatgacctgt ggagagtgct tggagatgtc | 960 |
| acaatgatgc tgtttgggaa gggactatca cggattccg | 999 |

```
<210> SEQ ID NO 17
<211> LENGTH: 999
<212> TYPE: DNA
<213> ORGANISM: Artificial sequence
<220> FEATURE:
<223> OTHER INFORMATION: Synthetic polynucleotide

<400> SEQUENCE: 17
```

| gctggagctg atttctgtgt gatgttggat gttcccaaac attttaagaa ctgtaatatg | 60 |
| ggtctgtaat gacctttgaa ataagtttg gtttgttttg aactctattg tcccatcaat | 120 |
| gttactactg tttgttatca atgtgtggaa ctgatatata attatcaact ctatgttggc | 180 |
| ctattgtgtt gaattttgtt ctgaattggc gtatattagt ggatttttta ttcttcaagc | 240 |
| ttgtcacgga ggaaaaacag ggatgagttg taaggatggt gatcatccca cgaattagat | 300 |
| tttggtatag taggtaaaag atattattag gtagggagaa cttttggatt agattctaaa | 360 |
| gtgatattat ggaaacgcat taaaggattt tgaacaaatt gagatcatga tccctagttt | 420 |
| caattagctg cccattacct agattttata catatgtaag ctatctgcta gagttggaac | 480 |
| attcatcaga atcggatccg tttaacagat aaaaacaaaa gcgattgggt taatcccatt | 540 |
| tttacagata acaacgcagg tttatacatg aaacaaatgt cattaccaag tgatattttt | 600 |
| ctgctctata ctctataccc tttttattat cattaatttt gtaattatat ggattaatta | 660 |
| aaggttcctc ccagagttaa attgttgtgt tggggtgcgt gtagagcttc tcttccaaca | 720 |
| agagacaagc ttgagatcac ggagtaacct gtcccttaac gtgctctttg tgcaagggtg | 780 |
| gcattgaaaa tacatttcac gtgtttgcag tttacccgag gatcatggaa tgctggcaga | 840 |
| agttggggtt gagtagcaaa gttgataatt taattatgca ggtgcagtct tttgctgaat | 900 |
| tcttcttcaa actcatgctt cctattgaat cttatcaaca atgtagagta gctatgacct | 960 |
| gtggagagtg cttggagatg tcacaatgat gctgtttgg | 999 |

```
<210> SEQ ID NO 18
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 18
```

| ggccattcat tccacaccgc tctgtgctga gagtttttg agcgttgccc ttataatatg | 60 |
| tctaatatat ccataatttt tccacgtctc ttactctgtg tgtgtgtttc tctcctcttc | 120 |
| ctcctatttt gttatttgta tgttcttttg taatttttta catgatcaac taaaaacatg | 180 |
| tactctctgt ttgtatgccc tacccatgtg tctcttaata tcaatataaa gaagagtgtt | 240 |
| caagttaatg tttggattcc aatgcttctc tcgatgaact cgcgtgcatt tttttaaata | 300 |
| cttattgttt ctcccaattc cgaaaagttc gagctgcaaa tttggacaga tgataaatgg | 360 |
| taggcaagtg tggtgttgtt tacataaaaa ctgctaaaac taaggtgtta atattactg | 420 |
| gtcatgtaag atattgtttt ctaagtttat atttagtagt aaataatagt tacactatta | 480 |
| aacaaagtaa aaccttttaa aaaaaataaa caaagtaaat catatttgt cacgtctttc | 540 |
| agaaacaaag ctactgacat ttttacttg ctaattattg tagtatcatg ttattgttgg | 600 |

| | |
|---|---|
| ttttcgttta cttcccgtct tcatcaccat tggtattgag aaaacaagtt tgaacaatgt | 660 |
| gcacatttcg agaacaacga ccacttgatt aagtactagg tcaaatttca gggagtaata | 720 |
| atttattatt tctcatttaa ttttatgatt tatttttgt ccgaaaaata ggaaatcttc | 780 |
| tctaaaattt attaatctat tgattggtag accatcgtgc tgctatggcc cctaatatat | 840 |
| aaaatgtgac ttctgaagtg gtatgatggt tttttttttt cttgtttatg taagacaagg | 900 |
| ttcggacaga tgcagatttt acattaacaa taatcctctg tttgtttgta gacttgtagt | 960 |
| ggaaaaaaaa atgaacaaat aagattcaat attgtatttt | 1000 |

<210> SEQ ID NO 19
<211> LENGTH: 1001
<212> TYPE: DNA
<213> ORGANISM: Artificial sequence
<220> FEATURE:
<223> OTHER INFORMATION: Synthetic polynucleotide

<400> SEQUENCE: 19

| | |
|---|---|
| gggcttgatg tcgttgatta gggtttatga ttatgctcag taattttagt tgtgtttgag | 60 |
| tttgagtatc tttatggttt tgtgtcaccg tggttcttgt ttttgaccaa tatatctggt | 120 |
| tgtttatagt cgatttaatg aaatgataat cagaaattgg agtatcgaag ttctaatgat | 180 |
| ttttactatt tgtgcgctgg atgtggaaaa tcttctgttt cacgaatgcg tgtcttgtta | 240 |
| ttcttcttca gaacacaaca ggctaagcag ccttcaaaac aataaggaa cttaattaac | 300 |
| aaaacctcga cggaaattta cctacagttt ttgcctgtga agataaaac cacaattttc | 360 |
| acgcccaatg ttctcaaagg attggggtct caagtgtgca gattggtgag aaaaatagat | 420 |
| acaacgagca tttttttgttc tgagaacatg aaatggtatt catcctttaa gtccgtgtgt | 480 |
| gtgtttatct ctgttcagac agtcagacct atgaattcat gaaacatgtc cagaaacatg | 540 |
| tccatcctct tgacttggtt ttaatttgat ggaaagcctg ctgatatcga gatgaacatt | 600 |
| attaaaagtc caattgtttc tacagaacta attgcaatcc tacgagatcg caagcaccat | 660 |
| gtcatggctt actatattat ttgaagaaaa aaaatcatag gctcagtgct tttcgacaaa | 720 |
| tagagcattg ttgattgtta agtcaatcgt gttttgggta tagggtggtc tcataacatt | 780 |
| tgtaggcagg attattctag caaatttttca aagtacttta taatccgaat tttgcctgat | 840 |
| tgctttgttg ttccacagaa gatacacata attgtatttc catgaactcc taaatagttc | 900 |
| tcaaggtagg caaggtaaaa gcgataccat ttttgattga tatccctatc aaaaacttta | 960 |
| tttcttattt taaagggaat tctttataac taatgatttg c | 1001 |

<210> SEQ ID NO 20
<211> LENGTH: 1001
<212> TYPE: DNA
<213> ORGANISM: Artificial sequence
<220> FEATURE:
<223> OTHER INFORMATION: Synthetic polynucleotide

<400> SEQUENCE: 20

| | |
|---|---|
| gagggggga aatgaaaata aaaaaaaaaa aattgtgtat tattgaatttt ctctggaatc | 60 |
| ttcttctgtg tatggttttc cttccttgtg ttttcttcct aattcacttt cgagggttgt | 120 |
| acttgttcct ttcgtcttaa atccttggat ggttgatgat catgaagttc tctttaaagt | 180 |
| taaattatta tcattttgtg catgctctct ctctctcact tggtccacaa caattgaatt | 240 |
| gaatgtagta tcattattcg ggtctggttg gttgtaccat ttcactagta cttcttactt | 300 |

```
tttcctgcat cctctctcga ttagaattaa aatatttctt tcttttctga agtttatgaa    360
tgattatact tgtgattttt gtgaccagtg tgttcatagc atattggtta aatatttatt    420
aaaaatcata atcaatataa tttcatgcat gtcaataaaa ttttttaattc cttaatcaat   480 attttaaaaa tattagttag catttaacca aagaataaaa tatattaaaa gtataaaacg    540
gttaatcttg ctatgcgaca aaatgtccta attatagaat cgctcgagca catgctacga    600
gtgggtccac cagtgtggat gggtaattgt aattcacttc cctaatgaag acaaattaaa   660
tgcgaggaag aatgaatgta aacgttgat agagaatgga ctgaacaaga ttgaagcata    720
tcatatagct atgcacctct tattggttgt atttctgtgc taattaaatt acaaacaagt   780
gaacacgtgt ttgagagtaa ctagtatgtg tgttcaagtt cgggaatgca tcctttagag   840
gtttcaattc gaaacattga atatataata atataagaat tggatagacg caagattttt   900
atatgataac attaagtgaa aactgtatgt atgcaatat gatattcatt tagattcaaa    960
ttatcactgt actgctttat ttcccctgt atcattgcca a                       1001

<210> SEQ ID NO 21
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 21
gccgcagcgc gacgtggagg aaatgcgcga tggtaggggt tgggtggttg gttgcgtggt    60
ggtcggggct atggtggtga tggcacgcgc gatggtgaga gggtgatgtt tggttgtggg   120 ttttgacct cacggccccc ttcgatcgcc aacttagcga tgccttcaag gtccttgact   180
actccaccga ctatgtcgtc gtctccgagc tctgccacat cctctccgag cttctgtcaa   240
ttctaagttt ttaccaaatc tgagttgcga tttctgtgat gcatgttgtg ttttttctca   300
tctaattctt aacatctggt tcttatgttt tgtcgttcct ttcaatgatt gtgtttttta   360
ttttgatttt tggggctgta gttgaatggc attcgatgaa gatgaaaagg ttggggaaga   420
ggaataaaaa tttgtggcga cttttttatat tttgtgataa ttttttaatct ataaattatt  480 tttaaaaaat tatattaaaa aataacatct tttaattttg tgataaaaat aacatatttt   540
gacatttatt aaataattaa tatacaatta aaaatattta atactagtat aataatggga   600
gtagtaggag ggaggcagtg gattgagttg agagtcataa ataaacaggt ggcaagaaga   660
gaacagagat ggcatgcaag tatgcaatat ttgcaatcaa gtcaaaatga gagttggcca   720
accccaaagg ctgtagtagg taagcatggc ccattttagt ttttacactc acctctcatt   780
ttcacctcaa ccacttctgc ctccttgcac atccactcaa cggttcagat tcaatctgac   840
tccccaatct cagccgtgga ttcaaatgcc acctcaggca catgcaattg caattgcaaa   900
tggatgaaca taacccacaa tctaatcttg ttacttaggg gcttttccgt cattaaatga   960
caccacccac cccctttttcc ctataaatgg caactcagtg                       1000

<210> SEQ ID NO 22
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 22
ttcaatcaaa cggttcatgc ttaatcaagt tgggaacaac aaaaaagtca aaacaatgtt    60
```

```
tgtgggtttc ggtttcattt catcaagatg atctgtttat ctttcttttt ttaaatttta      120
atttaaagtc tttgtatttt gtatgtaaag atgtaaaatt atgattatta ggtggtgcat      180
gtgtcgcgtc atgggccaat gttatcctca gctttaagt tggaagaggc ccaactcatg       240
tgtgatgtac ggctgtgatt gtgtaattgt caaaatcaaa ataaccccc gagtcatata       300 tgcatctttt tattttatct tattattaac atatatatat atatatatta atacctttta      360
aaattatgat gattatctct aaaacaaggt ctgaccataa ttttccaaa ttgctttacc       420 tttattagtg attttatagc tgattttggt tcatctctta gaattgattt tggttcagct      480
cacggtaatt ccaaacatcc tatatattgc tactactttta ttttctctag acccccctat    540
atgtcttctc tctaagattt gtcctcttca tcgaagtata tgccaaggtt gggtttcttt     600
atccattcct gtcagtcctg tgcccgttat cacttgctat ggatgattga atccggga       660 gagtgaggag tggggttggt ttagggtggg tgggtgggtg gatgatgtct attgcttaaa     720
tatgggacca cttttcttcc tcaataatgc acatattcta gtgttgtcca tttaataatg     780
attcgtgatc atagccttgg gaaaaaaacg tacactattt tttatttttt gtgctaaaat     840
ttggacaagc ttgatcttat cagcttcggc ggggaatgcc acttccttct agttacttcc     900
atggaatcct tcacggaaaa gacgtgggtg gcacttgtgg gatgggtaac tgagtagaaa     960
acattagtaa tttgacacgt ataaatcgtt gactcattct                           1000

<210> SEQ ID NO 23
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 23
atcgtgcgga ttggttcatc aggggatgtc ctttcttgtg gttacattaa atgttggttt      60
cttgctcttg tgtcttcgtt tctaggtagc ttgttttcg gacatagttt gaagtctcca      120
ccatcatctc gcaacttttg ttcccagaat tgggttcttg atcgacggtg gcaagacttc     180
ttttattatt ctgtgttttt gtgtttgtga gaacccctgc ccctgattac attttgtta     240 agcgcagcga ttttaggac ttttgctgtt gcgttgttgg tttgttttt aaattttaac       300 tttatatttg tgttcaattt tggcttggtt tgcttttaca atatcaactt atactttgg    360 tgtcaaattt tggctttgga tattttaact aacggctgtt gttttttctt cccatgttat     420
gatttgtctg ccgggaagat gcaagaatct taaatctttt actaaaagta aacgtgcttt     480
gacgacgggg aaccatattc gagtccttga tatttggtag tttgttttta tttttagttt     540
gaagaatata atttgttgac atttataat tgattgagaa ggtataattt gtattttata      600
ctatcgggat tttcttttaa ttgaatggag tttttttcaaa aatggatgat atataggaat    660
tgaatttgaa tttgtatcat agggcatagt gatgtgatta taattatatt ttcttggtgg    720
ttaatcgttt tcttaggatg aaaacatttt ttttttcttt gatgtgttgc attatcttaa    780
atgaatttct tgtttctaga taaatcttaa atgaatttt aactgtggta catcaacatg     840
taattgacat aacgcgtaaa cttagaaagt ttgtaggttt caacaagata tgaagaatga     900
aacaaactag aataaggatt ctatttttat acaattaatt aaaattctcc cctagatctt    960
tcgaatagaa atgtttaata ttctctcctt ttctataaaa                          1000

<210> SEQ ID NO 24
```

<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 24

| | | | | | |
|---|---|---|---|---|---|
| atcgtgcggg | catcagggga | tgtcgtttct | tatggttacg | ttaaatgttg | gtttcttgct | 60 |
| attgtgtctt | cgtttctagg | tagcttgttt | ttcggacata | gtttgaagtc | tccaccatca | 120 |
| tctcgcaact | tttgttccca | gaattgggtt | cttgatcgac | ggtggcaaga | ctccttttat | 180 |
| tattctgtgt | tttaatgtgt | ttttgtgttt | gtgagaaccc | ctgcccctga | ttacattttt | 240 |
| gtaagcgcag | cgagttttag | gacttttgct | tgttgcgttg | ttgatttgct | ttttaaattg | 300 |
| taactttata | tttgtgttca | attttggctt | ggtttgcttt | taaaaatatt | aactttataa | 360 |
| tttggtatca | aattttggct | ttggatatt | taactatcgg | ctgttgcttt | ttattcccat | 420 |
| gttatgattt | gtctgcggga | acatgcaaga | atcttaaatc | ttactaaaag | taaacgtgct | 480 |
| ttgacgtttg | aagaaaataa | tttgttgacg | ttttataatt | gactgagaag | gtataatttg | 540 |
| tgttttatac | tatcgggatt | ttctttcaat | tgaatggaga | ttttttttctt | tcaaaaatgg | 600 |
| atgatatata | agaagaattg | attttggact | tttatttatt | actaattttg | ataaaactac | 660 |
| ttttattctt | taaagcatat | gttaaaatta | attttaatca | tgtatttcag | tgtaagcatg | 720 |
| ggaagagtaa | gtttgatggt | ttagtgaaaa | ccaggctaag | aataatataa | tcccctttta | 780 |
| aattagacct | tttttttatt | aaggccacca | gaatctatac | tccgccgatt | acaaatgcca | 840 |
| aatccgatat | ttaaccgttt | tgaatttgta | tcatagtgca | tagtgatgtg | attataatta | 900 |
| tattttcttg | gtggttaatc | gttttcttag | gatgaaaaca | tttttttttct | ttgatgtgtt | 960 |
| gcattatctt | aaatgaattt | ttttttttata | gataaatctt | | | 1000 |

<210> SEQ ID NO 25
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 25

| | | | | | |
|---|---|---|---|---|---|
| aatgattata | gaaaatagta | tgctttctgg | tgggagcagc | actccttaag | ccttagttac | 60 |
| tcatatggaa | aatatcctag | tttgtgggat | ggtcaacttg | ggtagttatg | gtcccaaact | 120 |
| ctcaattttc | caagttgtgg | cataaattct | attgcacctt | ttaacaagct | ttgcttgttc | 180 |
| cagtgtgttt | tattatgatt | tgtgatttat | acaaccttgc | gtttgagtgc | cattttagtc | 240 |
| gtcttatccc | ttactagttg | aatttgtaac | tgttatgtgt | tatcagacaa | aaattggggg | 300 |
| ttcttcactt | attgacactc | gtcatccact | aatgttttgt | gactgtgact | tcttctggcc | 360 |
| gatatatgct | ttcttttgta | tgggcataca | aaggcctctt | gttcatgcta | tattcctttt | 420 |
| ttgttctatg | gtttgtggtg | gaatgaattt | tattcaactg | gttggttgtt | cttgaaacca | 480 |
| gagtgtactt | cattcgtagc | aatagcatct | aagcggttaa | tggtcatgct | ttatgatact | 540 |
| agtagcactt | gtgcagttta | ttgctctttt | ggccaatatg | cacttgtgga | aaatgctttt | 600 |
| ttcagatatt | gatccatact | tcttaacatt | tcgttttgga | gtgtaggtag | ttggaaagat | 660 |
| gggaaaaagg | agagaaaatg | acagatatgg | taaataaatt | atttaaatac | attttttggtc | 720 |
| tatataattt | agtattttttt | aaattttgtt | tttggaagaa | aaaaattagt | tcttgtaaaa | 780 |
| taggattgtt | ttattttttg | tttttaaatt | gttttagata | agatttgttt | tcctgcctaa | 840 |

| agtattttt attgtttaaa ctttaaagag ttatctaaaa tacttaaagg ataaaaaaaa | 900 |
| tcaatacatt ttatatgaat taaaaaaaat acaggacaaa aataaaataa aaaattataa | 960 |
| ggatcaaaat tatatttaga cccaaataaa gtgataggaa | 1000 |

<210> SEQ ID NO 26
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 26

| atcgtgtggg ttggttcatc aggggatgtc gtttcttatg gttacgttaa atgttggttt | 60 |
| cttgctattg ggtcttcgtt tctaggtagc ttgttttttcg gacatagttt taagtctcca | 120 |
| ccatcatctc gcaactttttg ttcccagaat tgggttcttg atcgacggtg gcaagactcc | 180 |
| ttttattatt ctgtgtttta atgtgttttt gtgtttgtga gaaccccctg cccctgatta | 240 |
| cattttgta agcgcagcga gttttaggac ttttgctgtt gcgttgttga tttgcttttt | 300 |
| aaattttaac tttatatttg tgttcaattt tggcttggtt tgcttttaaa atattaactt | 360 |
| tgtaatttgg tatcaaattt tggctttgga tattttaact atcggctgtt gcttttttcttt | 420 |
| cccatgttat gatttgtctg cgggaagatg caagaatctt aaatcttact aaaagtaaac | 480 |
| gtgctttgac gtttgaagaa aataaatttgt tgacattta taattgactg agaaggtata | 540 |
| atttgtgttt tatactatat tatcgggatt ttcttttaat tgaatggaga ttttgtttt | 600 |
| tcaaaatag atgatatata agaagaatgg aatttggact ttaattataa ctaatttga | 660 |
| taaaactact tttattcttt aaagcatatg ttaaaattaa ttttaatcat gtatttctgt | 720 |
| gtaagcatgg gaagagtaag tttgatggtt tagtgaaaac caggctaaga atattataat | 780 |
| ccccttttaa attagacctt ttttattaag gccaccagaa tctatactcc gctgattaca | 840 |
| aatgccaaat ccgatatta accgttttga atttgtatca tagtgcatag tgatgtgatt | 900 |
| ataattatat tttcttggtg gttaatcgtt ttcttaggat gaaaacatttt tttttctttt | 960 |
| atgtgttgca ttatccttaaa tgaatttctt ttttatagat | 1000 |

<210> SEQ ID NO 27
<211> LENGTH: 1001
<212> TYPE: DNA
<213> ORGANISM: Artificial sequence
<220> FEATURE:
<223> OTHER INFORMATION: Synthetic polynucleotide

<400> SEQUENCE: 27

| aattttcctc cccttgtcta tgatcgagga agaaaatctg taatatatta tgcaaaaaat | 60 |
| aattaaggtc ttttcctta aatgggctgg ttcaatgaac cgagaccact gcaggttcat | 120 |
| ggggatggga ggattaagag gctatgtttt ttaatcttcc gatgttactg ttgtttttt | 180 |
| tttaatttca ataaggatat tatatatgta gtactatgca agtagcttag agttgggtag | 240 |
| aagggcatgt tcatggtgtt aattatgtta tgtatgcgtg tgagtgctgt tatgatggca | 300 |
| gtgacaatgc ttatgatatt catactcata aagctaggtt gttctttcta aataaataaa | 360 |
| tcatggccca tgggcattat acactgttaa cactcgtatt agcataggcc cgaggataga | 420 |
| gacttgagga aacaagtttt aagtatccaa ctagtaacaa atgaataatc ttttaaatta | 480 |
| atgttatttt attttaagtg tgggttggca aacagattaa gcaaacaata tgtataattg | 540 |

| | |
|---|---|
| cggactaaaa taattgccga tagatactag tataggtggg ccaaaagaa ggatgaagta | 600 |
| aacaaaagag gtccgttgat gtgggccaaa ccaatttcac atttgaaaga taagaaaaaa | 660 |
| cttttgtaca cgcggaactt tgcactggat taggtgcagt gcagtactaa ctgttttcat | 720 |
| cgaaaatgac cattagcaat aacctgcaag ggagaaaatg ccaaaatgaa atcacgttgg | 780 |
| atcagctggt gctgtcctag ctattattcc tatgtttctg cacggaaaac taccgtttgt | 840 |
| attcgaatga gcaatgagaa atgacaaaga gcctatctct agattctttt cttgttggtg | 900 |
| attcttgata agtttatttt gtaaatagcg ctgcaagagt atgaagccta gccaaatatg | 960 |
| atcatatata tattgtcaat attatgtttc tcaaaaaata g | 1001 |

```
<210> SEQ ID NO 28
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 28
```

| | |
|---|---|
| gtaattcatt ccactgctct gtgctggag ttttttgagc gttgccctta taatatgtct | 60 |
| aatatccata aatttccacg tctcctactc tgtgtgtgtt tctctcctct tcctcctatt | 120 |
| ttgttatttg tatgttcttt tgtaatttt tacatgatca actaaaaaca tgtactctct | 180 |
| gtttgtatgc cctaccaatg tgtctcttaa tatcaatatc aaaagagag tgttcaagtt | 240 |
| aatgtttgga ttccaatgct tctctcgatg aactcgcgtg cattttttta aaatacttag | 300 |
| tttctcccaa ttccgaaaag ttcgagctgc aaatttggac agatgataaa tggtaggcac | 360 |
| gtgtggtgtt gtatacataa aaactgctat aactaaggtg ttaaatatta ctggtcatgt | 420 |
| aagatattgt tttctaagtt tatatttagt tgtaaataat agttcacacta ttaaacaaag | 480 |
| taaaacattt aaaaaaaaca aacaaagtaa aacatttttaa aaaacaaac aaagtaaatc | 540 |
| atattttgtc acgtctttca gaaacaaagc tactgacatt ttttacttgc taattattgt | 600 |
| agtatcatgt tattgttggt tttcgtttac ttcccgtctc catcaccatt ggtattgaga | 660 |
| aaacaagttt ggacaatgtg cacatttcga gaactacgac aacttgatta agtactgtgt | 720 |
| caaatttcag ggagtaataa tttattattt ctcatttaat tttatgattt atttttttgtc | 780 |
| cgaaaaatag gaagtcttct ctaaaattta ttaatctatt gattggtaga ccattgtgct | 840 |
| gctatggccc ctaaataaaa tgtgccttct aaagtggtat gatggtttct ttttttcttgt | 900 |
| ttatgtaaga caaggatcgg acagatgtag attttacatt aacaataatc ctctgtctgt | 960 |
| ttgtagtgaa taaaaaaaaa aacaaatgaa caaataagat | 1000 |

```
<210> SEQ ID NO 29
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 29
```

| | |
|---|---|
| ggcttgattt cgttgattag ggtttatgat tatgctcagt aatttagtt cttgtgtttg | 60 |
| agttcgagtt tctttatggt tttgtgttac cgtggttctt gttttgacc aatatatctg | 120 |
| gttgtttata gtcgatttaa tgaaatgata atcagaaatt ggagtattga agttctacac | 180 |
| atttttactt tttgtgtgct ggatgtggaa aatattctat ttcacgaatg cttgtcttgt | 240 |
| tgttattctt cttccgaaca caacaggcta agcagccttc aaaacaaaaa aaacaactaa | 300 |

```
attcacaaaa cctcgacgga aattttccta cagttttgcc tgtgaaagag agagacacaa    360
ttttcacgcc caatgttctc aaaggattgg gttctcaagt gtgcagattg gtgagaaaaa    420
tagtacatcg aaatcgaaca ttttttttct gagaacatga aatgatattc atcctcaagg    480
ccgtgtatat gtttagctat gttcagacct atgaattcat gaaacatgtc acatcctctt    540
gttgatttta atttgatgaa agcttctgat atccagagga acattattaa aagtccaatt    600
gtttctacag aactaattgc aatcctacgt gacagcaagc acgatgtcat ggcttactaa    660
aatattaaga aaaaaatca tagactcggt gcttttagac aaatagagca ttgttgattg     720
ttaagtcaat cctctctttt gggtataggg tggtctcata acatttgtag gcagggatta   780
ttctagcaat ttttcaaagt actttatatt ccgaattttg cctgattgct tgttgttcc    840 acaaaagata caaataattg catatttgaa ttgtagtgag tatagtttac tagtaaaagt   900
atgaataatt gtatatttga attgtagtga gtatagttta gtggtaaaag tatgattctt   960
tcatggactc gactcctaaa tagttaaggt agtcaagaaa                         1000

<210> SEQ ID NO 30
<211> LENGTH: 1000
<212> TYPE: DNA
<213> ORGANISM: Artificial sequence
<220> FEATURE:
<223> OTHER INFORMATION: Synthetic polynucleotide

<400> SEQUENCE: 30
gctgtttcaa tactgtggta gtgctataaa ttggcctact ttttgtttct tacagtctat     60
tagcctagca gccgttaggc ctctttttta aatgtaataa gttgaattcc tgaactcgtg    120
aagcttgccc cttattgaac cgtagtgttt ttggttgctt aataccatta agcattgagt    180
tgttttggat ttatttgcat ttaccgaatt ttatttggaa gatagtaagc gttttttcca    240
tgttcacaaa tatgccatga aaaagcagt aaaatttcaa taaccaaca tcatgataaa     300 acaaaagtat gcatcgtatg aaaaaaagtg ggtgatgaaa tgataagtct aattttggtc    360
gaatttggtc gttgttattt ttgcatgaac atctcttttg tacaacctaa caactaattt    420 gctatttta atatttttgt actgcttttg atttgcttgc tcttcacaat attatagtgt    480
tgcattagtt gttcaatttt ggttgtacaa ataatacaac ttttaagcag ttatcgtgaa    540
tgttagaaaa atcatgtgac ttatctctgt tattgggtga ttgcatttgt ttcgtgactt    600
gtctttaatc ggttacttat tttcaataat aaataacaat atagcattat tttgtgtcac    660
tttcttactt ttgattattg aaaagccgtg ctcctttgcc tgtctcttga gccatgtgat    720
tcgtcgtgaa ttgtgaggac gagatcatat ttgagaaaga aaatgtgagc tagacgtttc    780
tatagcttta ttacgtagcc cttgcaattc aattcagcag ggaacatatc aaaatgattt    840
gtattgaaaa aattgttcta cctacaaaaa tctactttat tatttgtact gaacgagaaa    900
gtgccacaat acttaattag ataagtgagc attggagcta atctcaaaat tcttgcctgc    960
tttttctatc atatatctcc atatcactaa ttaattcatt                         1000

<210> SEQ ID NO 31
<211> LENGTH: 2000
<212> TYPE: DNA
<213> ORGANISM: Artificial Sequence
<220> FEATURE:
<223> OTHER INFORMATION: Synthetic polynucleotide

<400> SEQUENCE: 31
```

```
aaaactttca catgaatagc acgaagaatc acaatgaacg attgatcttc tttttaaaatc    60
aaatattaat tgggaaataa aaaaataaaa aatggaagtt cacaatatag tgttcgtgtg   120
cttttcatga aaactgtttt tgtaactttc agcatttttc atataattag gtcatgttgg   180
gtataattag ctataaaatt agttaaaaat ttaaaaatta gttggtaact taaagttaaa   240
aagtaactta ttaaattaaa aatattttaa taaaattaat tgttaaaata attgaaaagt   300
ataaaataac aaaaaataat aaatcaatta atttaaataa gataactagg aaaataaata   360
aaagattaaa aaaaactaaa aaactaaaaa actaaagttt taaataatgt ttaaaaatag   420
ttaaaaatta ttaaaaactt atttataaaa cagttaaatt ataaacaaac ttttcgctta   480
tgaaaaataa aagcttacct aactttagta gacaacttgt ccaacaatta gttgatacct   540
attgccctta agttttcttt aatatcaatt attggttttg tcaacaagct atcttttaat   600
cttaatttat tggtaaaaaa tccgtcgcct tcaagttaca tcatttaaca catctgctca   660
ttagaaaaat aaaattcttc ctaaacgatt agtagaaaaa atcattttaa taatgaataa   720
gaaagaaata ttaggaaaaa ataacttcat ttaaaaaaaa catttggatt atattttact   780
ttaaaatatc taaatatttt taaatgacta attttatata cactgtaact aaaagtatac   840
aagttattat gttatgtatc ataaagaaat acttaaaaaa tctactgaag aatatcttac   900
aaagtaaaaa taaataaga aataagttag tggaataatt atgattttat ttgaaaattg   960
aaaaaataat tattaaagaa tttagtggag taagaaagct ttccgattat tcttttttc   1020
cataataaaa aaatctagca tgacagcttt tccatagatt ttaataatgt aaaatactag  1080
tagcagccga ccgttcaggt aatggaccct ataaaatttc gaacgctcca ctccacttgc  1140
aacgagtgcg ggccccaatt taataacgcc gtcgtaacag ataaagtcca acgtgaagcg  1200
gtgaaggtgc atctctgact ccgtcaagat tacgaaaccg ctaattacga aggactcccc  1260
gaaaatgcat ccaataccga aatatcatgt gtgataagca ccaagtgaca ccatacatga  1320
gcacgcgtca caatatgatt ggagaacagt tccaccacat atgctataaa ttgcccccac  1380
accccctcgtc catcttcgca gttcaattcc aatcaaatta gttcattctc tttgcgcagt  1440
tccctacctc tccattcaag gttcgtaaat ttttctgtt tttctttttt cttttttttcg  1500
ttattgtttg ttcttcatca gcatgatgtt gatttgattg tgttctacat agtttcatcg  1560
aatcttaatt ttcataatca gaatcagctt ttattaatgc aagaactttt ttaatggatg  1620
attttacaat cgtatattag gtctaattag agttttttt cataaaaaat ttcagatccg   1680
tttacaacaa gccttaattt agattctgta gtcgtagatt agggtttttt ttttcattta  1740
ttacttcaga tccgttaaag aacagcctta tttgttgata cttcagtcgt ttttcaagaa  1800
attgtcagac cagttgaaaa aagcctgatt cgttgattct gtatagtttt tcaagagata  1860
ttgctcagat ctgttagcaa ctgccttatc tgttgattct atggccatag attagggggtt  1920
tttttctctc catgaaattg cttcttaaaa ctacgtgatg gattttgatt ctgatttatc  1980
tgtgattgtt gattctacag                                              2000
```

US 12,031,140 B2

GLYCINE REGULATORY ELEMENTS AND USES THEREOF

RELATED APPLICATIONS

This application is a 371 of International Application No. PCT/US2020/061749, filed Nov. 23, 2020, which claims priority to U.S. provisional Application No. 62/939,762, filed Nov. 25, 2019, the contents of which are incorporated by reference in their entirety herein.

FIELD OF THE INVENTION

The present invention relates to regulatory elements, e.g., promoters and terminators, which are useful for expression cassettes in plants, such as soybean.

SEQUENCE LISTING

This application is accompanied by a sequence listing entitled 82000_5 T25.txt, created Nov. 16, 2020, which is approximately 54 kb in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

Genetically modified plants are an important source of desirable traits, such as insect resistance and herbicide tolerance. In general, to create such traits, one or more nucleic acids are introduced into a plant containing expression cassettes that express one or more coding sequences for one or more traits. Such expression cassettes generally contain a promoter and terminator sequence to control expression of each coding sequence. For certain traits, such as insect resistance and herbicide tolerance, it may be desirable to use promoters and terminators with medium to high constitutive expression. The choices for such promoters and terminators remain limited. There remains a need for additional sequences for promoters and terminators that drive gene expression for robust protein production, ideally in all or most soybean tissues.

SUMMARY

Provided herein are regulatory elements, such as promoters and terminators, obtained or derived from *Glycine* species, e.g., *Glycine* argyrea, *Glycine* canescens, *Glycine* clandestine, *Glycine max* and *Glycine tomentella*. Such regulatory elements are useful for constructing expression cassettes for expression of a coding sequence of interest, such as expression of a coding sequence for a trait of interest in a plant. As described herein, several promoter and terminator sequences were tested and shown to have improved levels of expression in leaf, root, seed pod, and/or embryo compared to a control promoter or terminator. Accordingly, aspects of the disclosure relate to such regulatory elements and their use in expression cassettes, vectors, and transgenic plant and plant cells.

In some embodiments, the disclosure provides an expression cassette comprising a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-5, 8-29, or 31, wherein the nucleotide sequence is operably linked to a heterologous nucleotide sequence. In some embodiments, the disclosure provides an expression cassette comprising a nucleotide sequence comprising one or more of SEQ ID NOs: 1-5, 8-29, or 31, or a biologically active fragment thereof, wherein the nucleotide sequence is operably linked to a heterologous nucleotide sequence. In some embodiments, the disclosure provides an expression cassette comprising a first nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-5 and a second nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 8-29, wherein the first and/or second nucleotide sequence are operably linked to a heterologous nucleotide sequence.

In some embodiments, the heterologous nucleotide sequence is a nucleic acid of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process or altered reproductive capability. In some embodiments, the heterologous nucleotide sequence encodes a selectable marker. In some embodiments, the expression cassette further comprises a selectable marker.

In some embodiments, the disclosure provides a vector comprising the expression cassette of any of the above-mentioned embodiments. In some embodiments, the vector is a plasmid, virus, or *Agrobacterium*.

In some embodiments, the disclosure provides a plant cell comprising the expression cassette or vector of any of the above-mentioned embodiments. In some embodiments, the plant cell is a dicot cell. In some embodiments, the plant cell is a *Glycine max* cell. In some embodiments, the disclosure provides a transgenic plant comprising the plant cell. In some embodiments, the plant is a dicot. In some embodiments, the plant is a *Glycine max* plant. In some embodiments, the disclosure provides a seed from the transgenic plant.

In some embodiments, the disclosure provides a method, comprising introducing the expression cassette or vector of any of the above-mentioned embodiments into a plant or plant cell. In some embodiments, the method further comprises placing the plant or plant cell under conditions whereby an RNA or protein of interest and/or a selectable marker is expressed from the expression cassette or vector. In some embodiments, the method further comprises crossing the plant to a second plant or self-crossing the plant to produce a progeny plant.

In some embodiments, the disclosure provides a transgenic plant produced by the method of any of the above-mentioned embodiments, or a plant part thereof. In some embodiments, the plant is a dicot. In some embodiments, the plant is a *Glycine max* plant.

24276=prGmSAMS, positive control. The labels A010A, A021A, A027A, etc. each represent a different event.

Figure 2:
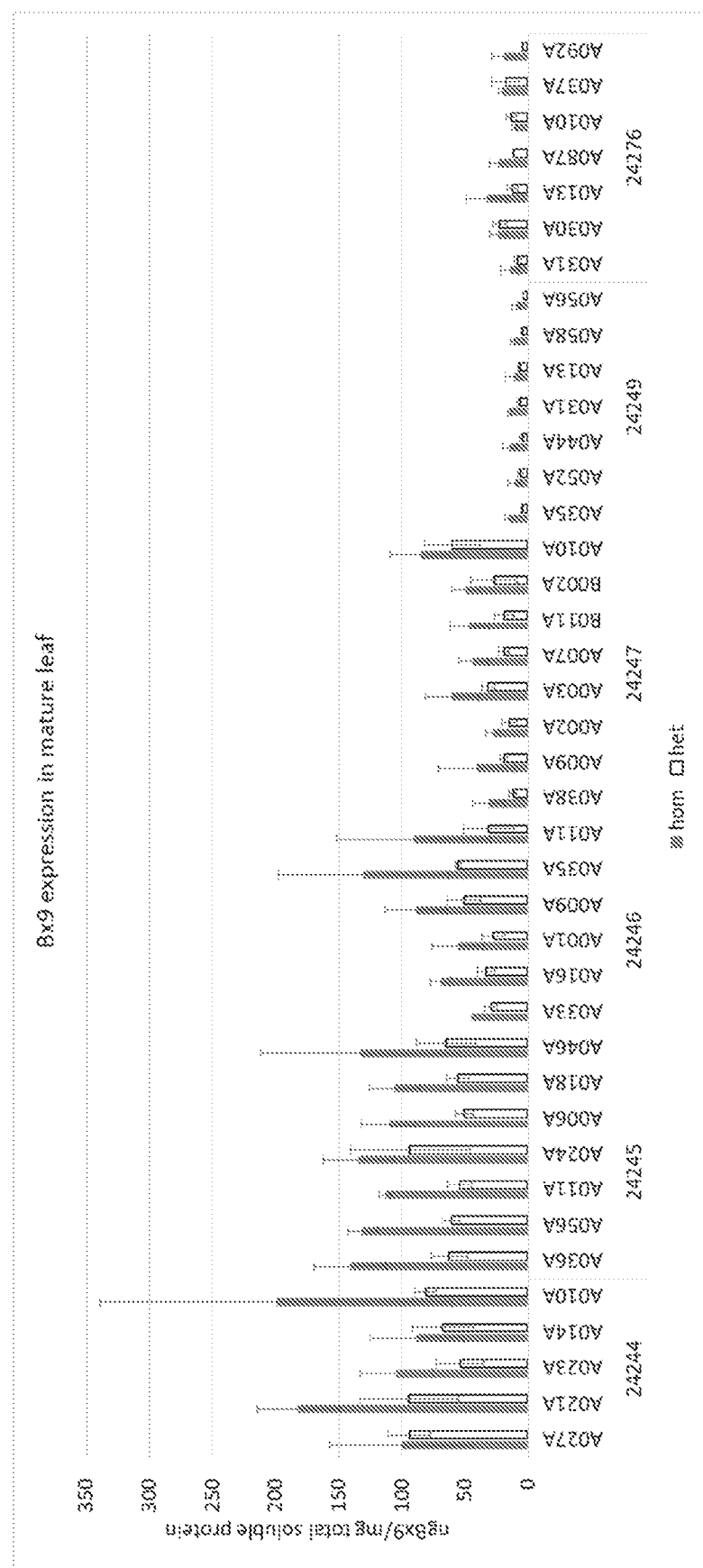

FIG. 2 is a graph showing Bx9 expression in T1 soybean mature leaf at reproductive stage. Hom=homozygous, Het=heterozygous. 24244=prGaUbi599400; 24245=prGcUbiPI339656; 24246=prGtUbiPI505267; 24247=prGaEF1aPI599400; 24249=prGaSAMSPI599400, negative control; 24276=prGmSAMS, positive control. The labels A027A, A021A, A023A, etc. each represent a different event.

Figure 3:
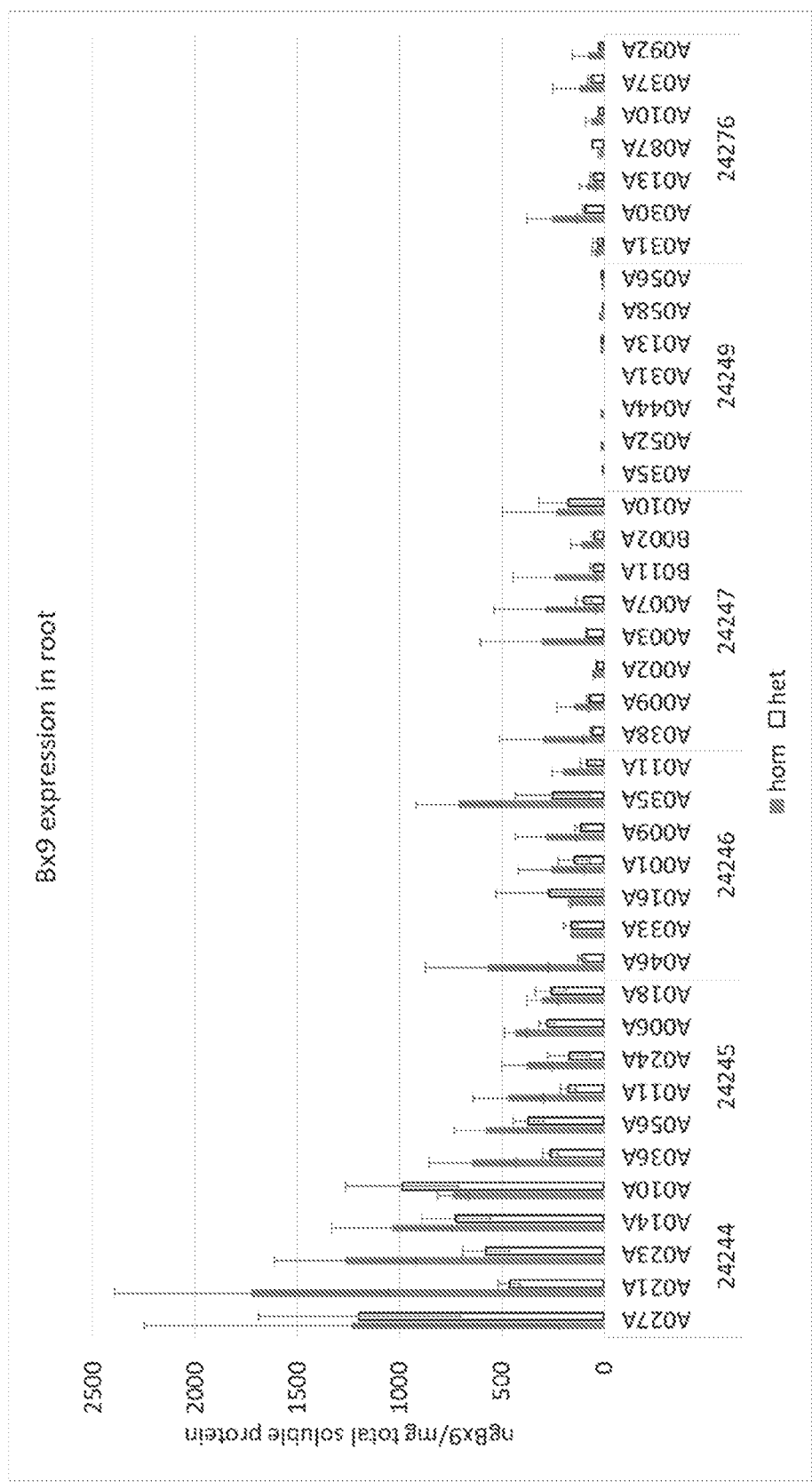

FIG. 3 is a graph showing Bx9 expression in T1 soybean root at the reproductive stage. Hom=homozygous, Het=heterozygous. 24244=prGaUbi599400; 24245=prGcUbiPI339656; 24246=prGtUbiPI505267; 24247=prGaEF1aPI599400; 24249=prGaSAMSPI599400, negative control; 24276=prGmSAMS, positive control. The labels A027A, A021A, A023A, etc. each represent a different event.

Figure 4:
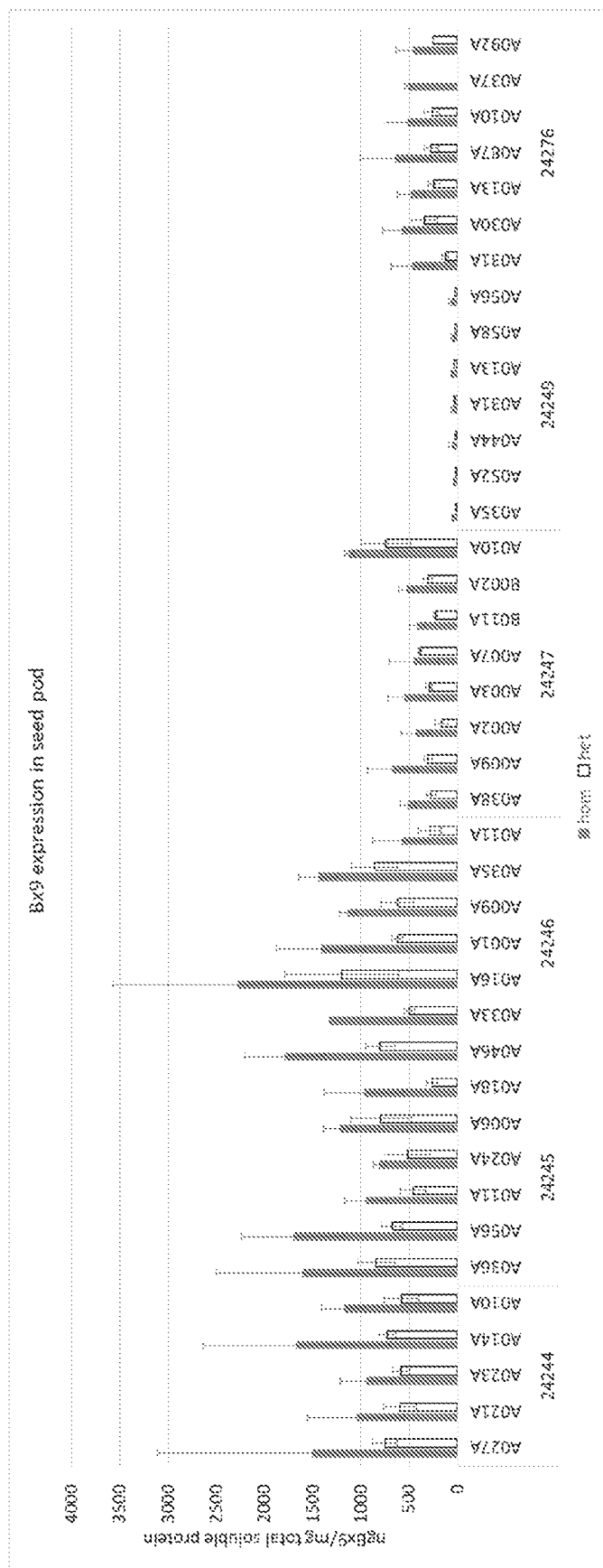

FIG. 4 is a graph showing Bx9 expression in T1 soybean seed pod. Hom=homozygous, Het=heterozygous. 24244=prGaUbi599400; 24245=prGcUbiPI339656; 24246=prGtUbiPI505267; 24247=prGaEF1aPI599400; 24249=prGaSAMSPI599400, negative control; 24276=prGmSAMS, positive control. The labels A027A, A021A, A023A, etc. each represent a different event.

Figure 5:
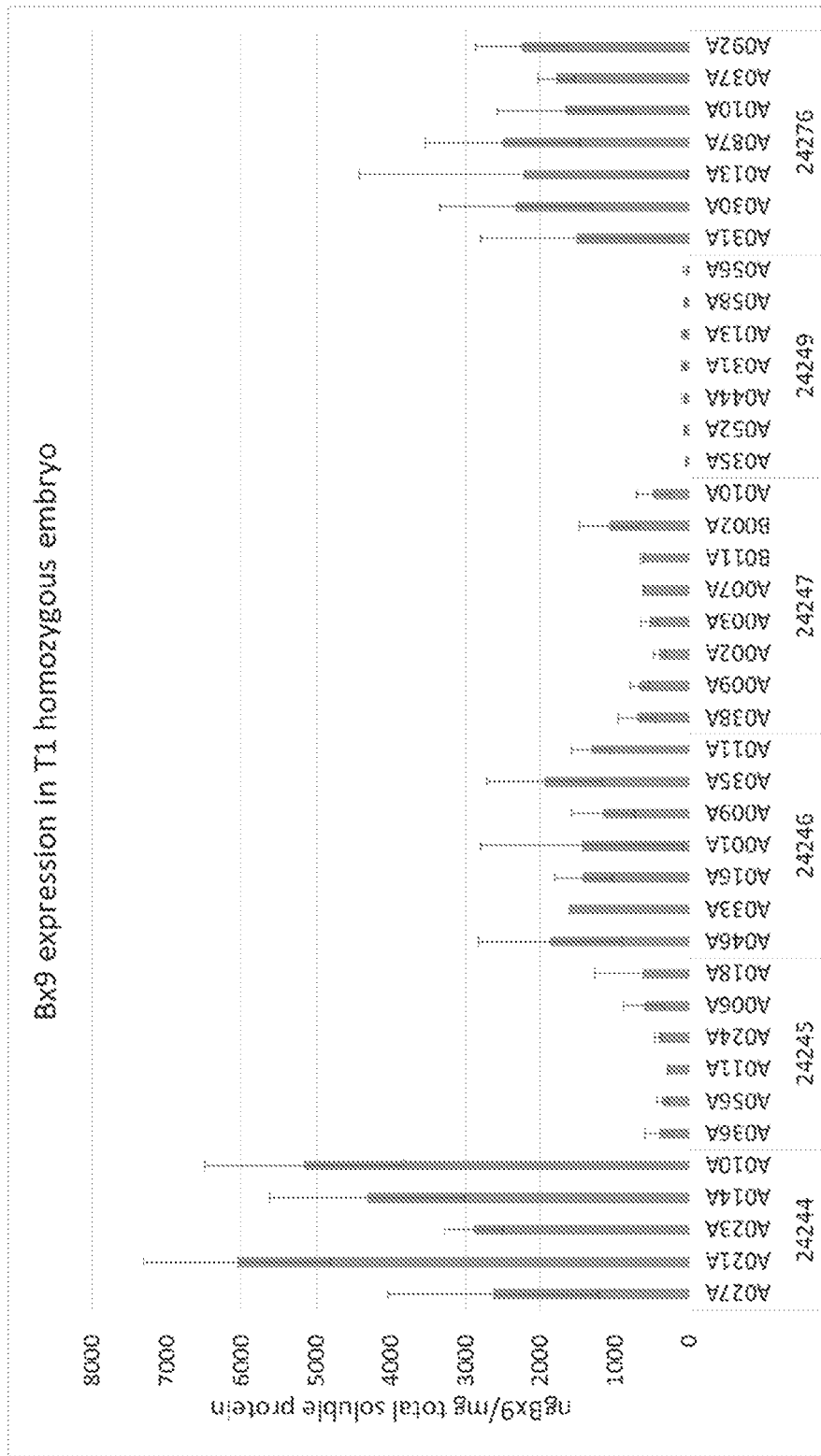

FIG. 5 is a graph showing Bx9 expression in T1 soybean homozygous embryo. 24244=prGaUbi599400; 24245=prGcUbiPI339656; 24246=prGtUbiPI505267; 24247=prGaEF1aPI599400; 24249=prGaSAMSPI599400, negative control; 24276=prGmSAMS, positive control. The labels A027A, A021A, A023A, etc. each represent a different event.

Figure 6:
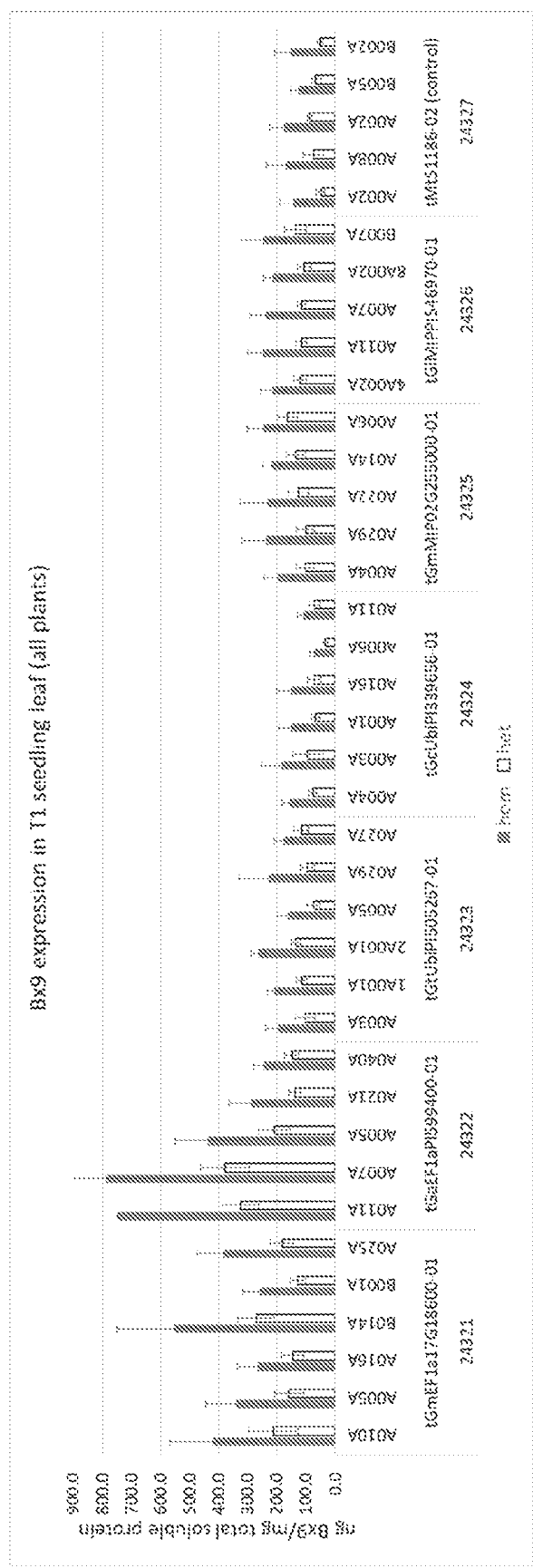

FIG. 6 is a graph showing Bx9 expression in T1 soybean seedling leaf. Hom=homozygous, Het=heterozygous. The labels A010A, A005A, A016A, etc. each represent a different event.

Figure 7:
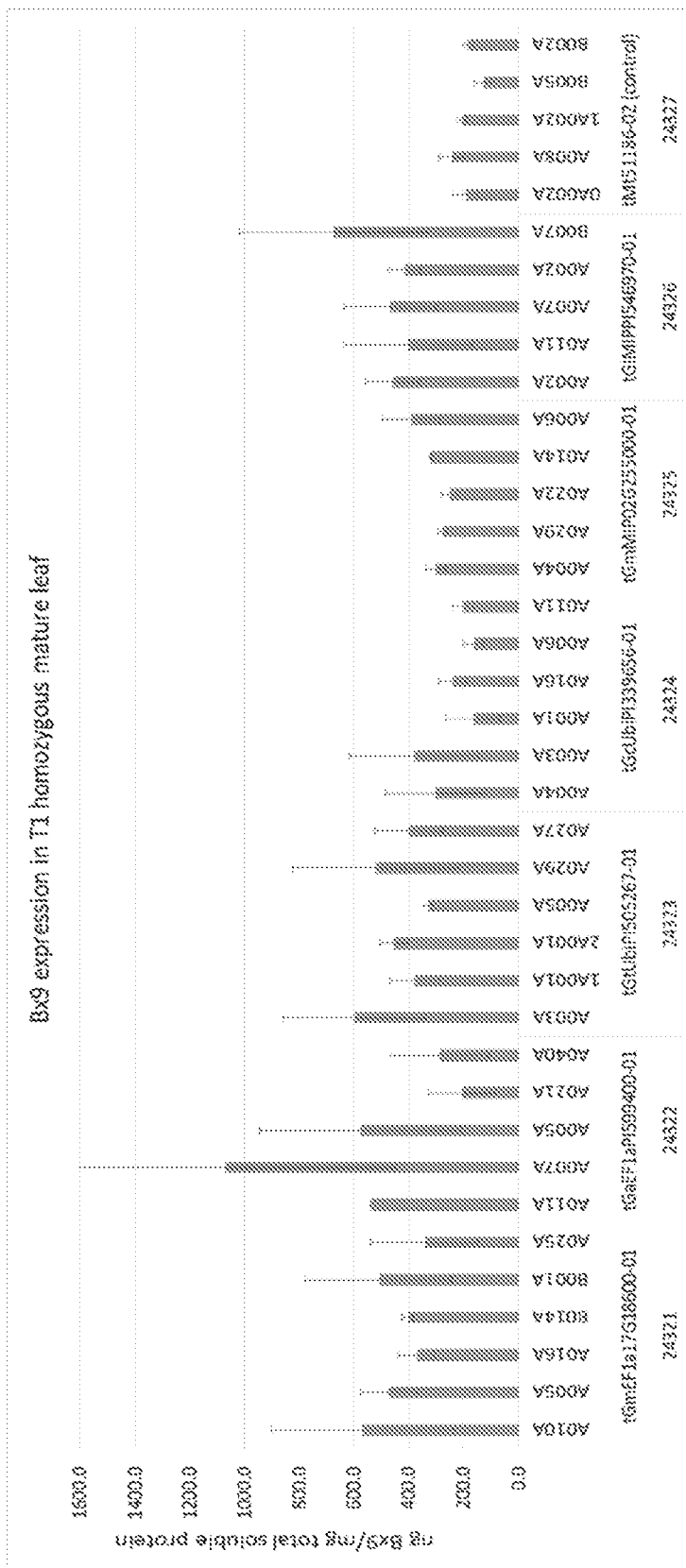

FIG. 7 is a graph showing Bx9 expression in T1 soybean homozygous mature leaf at reproductive stage. The labels A010A, A005A, A016A, etc. each represent a different event.

Figure 8:
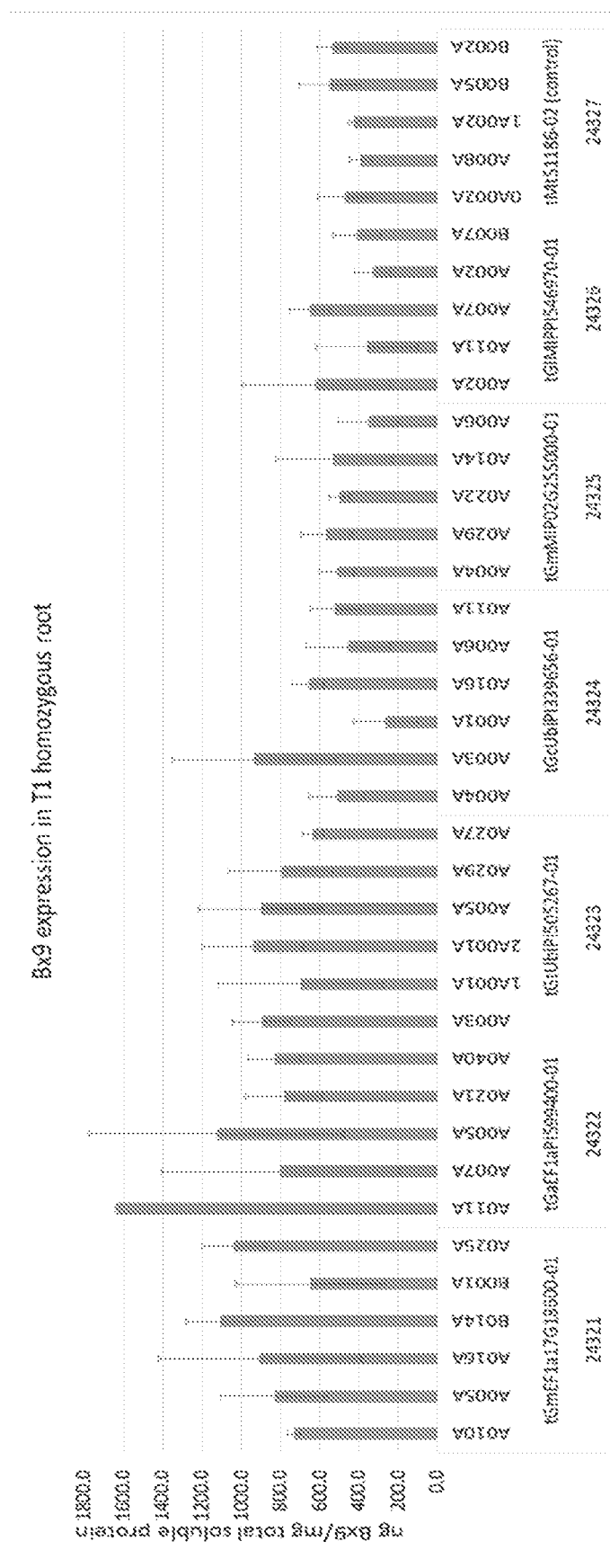

FIG. 8 is a graph showing Bx9 expression in T1 soybean homozygous root at the reproductive stage. The labels A010A, A005A, A016A, etc. each represent a different event.

Figure 9:
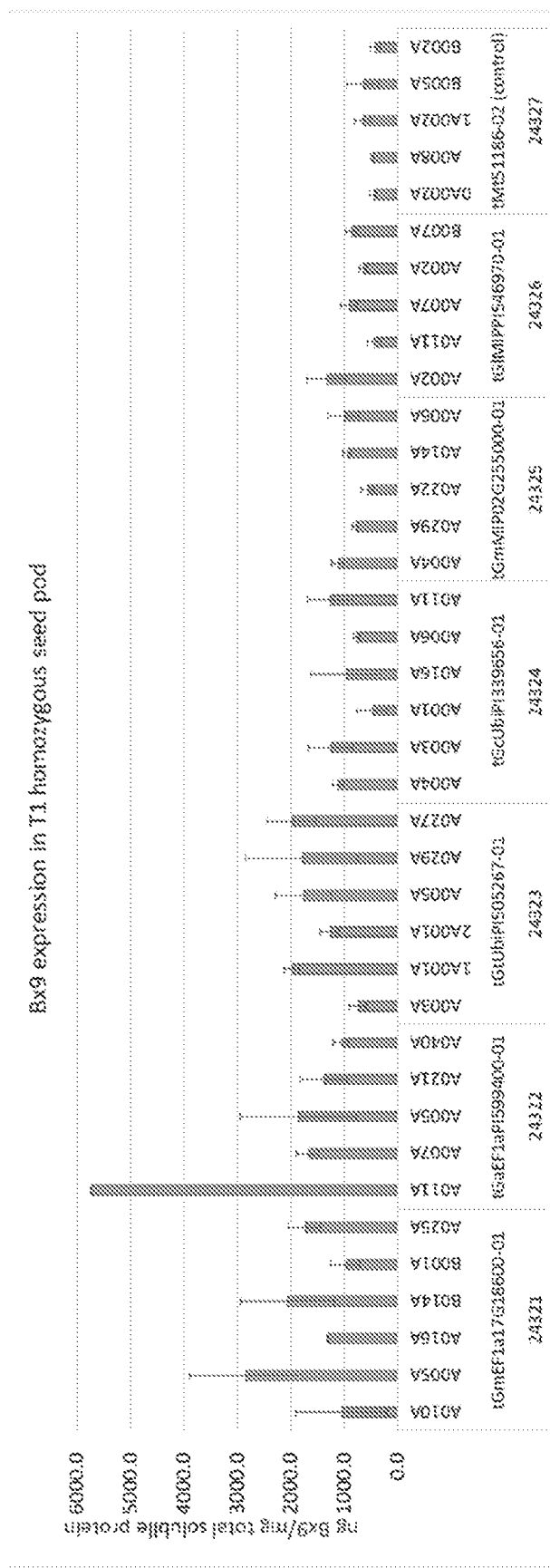

FIG. 9 is a graph showing Bx9 expression in T1 soybean homozygous seed pod. The labels A010A, A005A, A016A, etc. each represent a different event.

Figure 10:
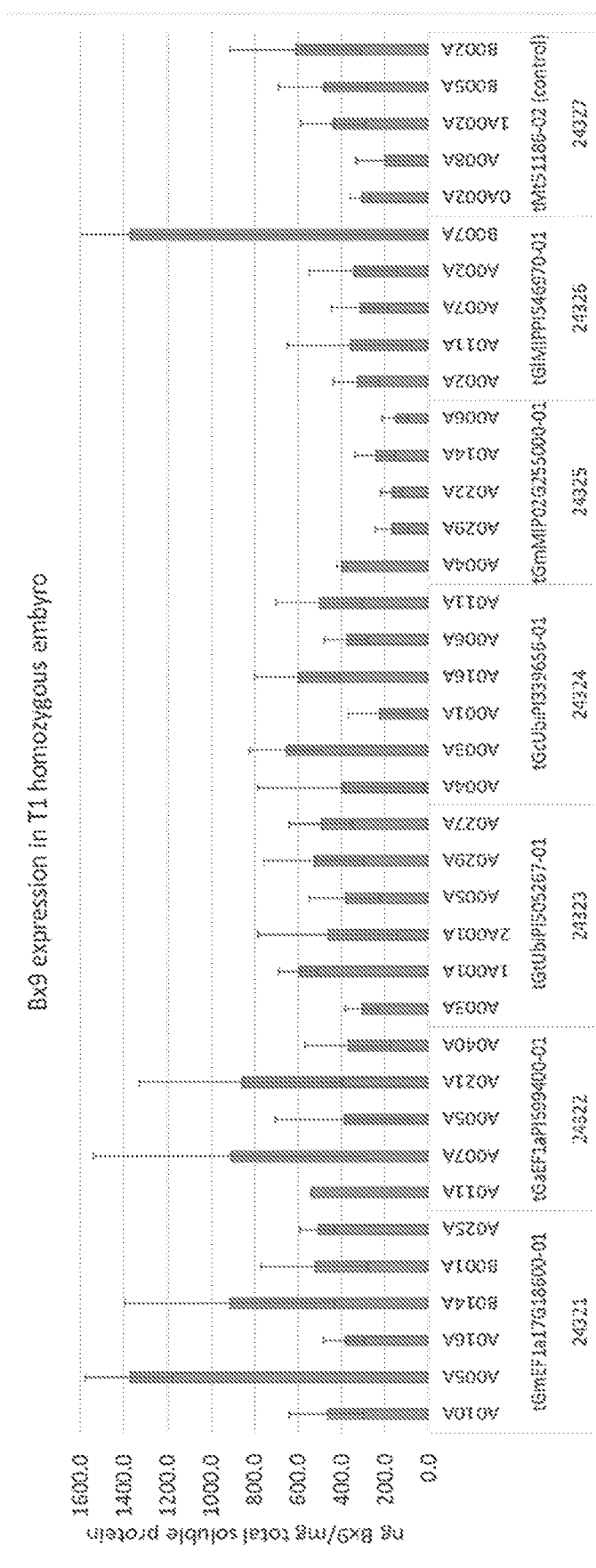

FIG. 10 is a graph showing Bx9 expression in T1 soybean homozygous embryo. The labels A010A, A005A, A016A, etc. each represent a different event.

BRIEF DESCRIPTION OF THE SEQUENCES IN THE SEQUENCE LISTING

SEQ ID NO: 1 is promoter prGaUbiPI599400.
SEQ ID NO: 2 is promoter prGcUbiPI339656.
SEQ ID NO: 3 is promoter prGtUbiPI505267.
SEQ ID NO: 4 is promoter prGaEF1aPI599400.
SEQ ID NO: 5 is promoter prGmEF1aGlyma17G186600.
SEQ ID NO: 6 is promoter prGaSAMS599400.
SEQ ID NO: 7 is promoter prGmSAMS.
SEQ ID NO: 8 is terminator tGmEF1a17G18600.
SEQ ID NO: 9 is terminator tGtUbiPI505267.
SEQ ID NO: 10 is terminator tGaEF1aP1599400.
SEQ ID NO: 11 is terminator tGmMIP02G255000.
SEQ ID NO: 12 is terminator tGtMIPPI505267.
SEQ ID NO: 13 is terminator tGlMIPPI546970.
SEQ ID NO: 14 is terminator tGcUbiPI339656.
SEQ ID NO: 15 is terminator tGtEF1aPI441001.
SEQ ID NO: 16 is terminator tGaUbiPI599400.
SEQ ID NO: 17 is terminator tGcUbiPI595799.
SEQ ID NO: 18 is terminator tGcSAMSPI339656.
SEQ ID NO: 19 is terminator tGmRBPGlyma11G117300.
SEQ ID NO: 20 is terminator tGmMIPGlyma19G186100.
SEQ ID NO: 21 is terminator tGaSAMSPI599400.
SEQ ID NO: 22 is terminator tGaMIPPI505151.
SEQ ID NO: 23 is terminator tGtEF-02PI441001.
SEQ ID NO: 24 is terminator tGaEF-02P1599400.
SEQ ID NO: 25 is terminator tGaADF3PI599400.
SEQ ID NO: 26 is terminator tGcEF-02P1483193.
SEQ ID NO: 27 is terminator tGmPDXGlyma07G260300.
SEQ ID NO: 28 is terminator tGtSAMsPI505267.
SEQ ID NO: 29 is terminator tGaRBPPI599400.
SEQ ID NO: 30 is terminator tMt51186.
SEQ ID NO: 31 is promoter prGaUbiPI599400-02.

Definitions

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications referenced herein are incorporated by reference in their entireties for the teachings relevant to the sentence or paragraph in which the reference is presented. In case of a conflict in terminology, the present specification is controlling.

As used herein, the terms "a" or "an" or "the" may refer to one or more than one, unless the context clearly and unequivocally indicates otherwise. For example, "an" endogenous nucleic acid can mean one endogenous nucleic acid or a plurality of endogenous nucleic acids.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above.

As used herein, a "biologically active fragment" refers to a fragment of a reference sequence that has activity that is substantially equivalent to (e.g., at least 90% equivalent to) or greater than the activity of a reference sequence. For example, a biologically active fragment of a reference promoter would be a fragment that is capable of driving expression of a coding sequence at a substantially equivalent or higher level compared to the reference promoter.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

As used herein, the terms "elite" and/or "elite line" refer to any line that is substantially homozygous and has resulted from breeding and selection for desirable agronomic performance.

An "enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g., if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

"Expression cassette" as used herein means a nucleic acid molecule capable of directing expression of a particular polynucleotide or polynucleotides in an appropriate host cell, comprising a promoter operably linked to the polynucleotide or polynucleotides of interest which is/are operably linked to termination signals. It also typically comprises polynucleotides required for proper translation of the polynucleotide or polynucleotides of interest. The expression cassette may also comprise polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular polynucleotide of the expression cassette does not occur naturally in the host cell and must have been introduced into the host cell or an ancestor of the host cell by a transformation process known in the art. The expression of the polynucleotide(s) in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

As used herein, the term "genome editing agent" refers to an agent that is capable of inducing a deletion, insertion, indel, or other modification in the genome of a cell, e.g., by creating a single or double-stranded break in the genome. Examples of genome editing agents include CRISPR/Cas agents (e.g., Cas proteins and guide RNAs), transcription activator-like effector nucleases (TALENs), DNA-guided nucleases, meganucleases, recombinases, and zinc finger nucleases. Cas proteins include Cas9, Cpf1 (also known as Cas12a), C2c1, C2c2, and C2c3, and functional variants thereof. Example Cas9 and Cpf1 proteins include *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), *Francisella novicida* Cpf1 (FnCpf1), Acidaminococcus sp. Cpf1 (AsCpf1), or Lachnospiraceae bacterium ND2006 Cpf1 (LbCpf1). A "variant" of a Cas protein refers to a protein or polypeptide derivative of a wild type Cas protein, e.g., a protein having one or more point mutations, insertions, deletions, truncations, a fusion protein, or a combination thereof. In certain embodiments, the Cas variant is a functional variant which substantially retains the nuclease activity of or has better nuclease activity than the wild type Cas protein. Example guide RNAs include single guide RNAs and dual guide RNAs.

A "heterologous" nucleic acid sequence is a nucleic acid sequence not naturally associated with a host cell into which it is introduced, including non-naturally occurring multiple copies of a naturally occurring nucleic acid sequence. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a translation start site or transcription start site of a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The terms "percent sequence identity" or "percent identity" are used interchangeably herein and is used herein refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned. Optimal alignment of sequences for aligning a comparison window are known to those skilled in the art and may be conducted using known methods, e.g., using known software or computer programs such as the Smith and Waterman algorithm implemented in the EMBOSS-6.6.0 water tool using default matrix files EBLOSUM62 for protein, EDNAFULL for DNA with default gap penalties. EMBOSS-6.6.0 is available, e.g., from the following Biosoft and Open-Bio such as at the following websites: en.biosoft.net/format/emboss.html or emboss.open-bio.org/html/adm/ch01s01.

The terms "nucleic acid" or "polynucleotide" are used interchangeably herein and refer to any physical string of monomer units that can be corresponded to a string of nucleotides, including a polymer of nucleotides (e.g., a typical DNA polymer or polydeoxyribonucleotide or RNA polymer or polyribonucleotide), modified oligonucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated. The nucleic acid can be present in a vector, such as in a cell, virus or plasmid.

"Operably linked" refers to the association of polynucleotides on a single nucleic acid fragment so that the function of one affects the function of the other. For example, a promoter is operably linked with a coding polynucleotide when it is capable of affecting the expression of that coding polynucleotide (i.e., that the coding polynucleotide is under the transcriptional control of the promoter). Coding polynucleotide in sense or antisense orientation can be operably linked to regulatory polynucleotides.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. A plant may be a monocotyledonous or dicotyledonous plant species.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Plant tissue" as used herein means a group of plant cells organized into a structural and functional unit. Any tissue of a plant in planta or in culture is included. This term includes, but is not limited to, whole plants, plant organs, plant seeds, tissue culture and any group of plant cells organized into structural and/or functional units. The use of this term in conjunction with, or in the absence of, any specific type of plant tissue as listed above or otherwise embraced by this definition is not intended to be exclusive of any other type of plant tissue.

The term "promoter," as used herein, refers to a polynucleotide, usually upstream (5') of the translation start site of a coding sequence, which controls the expression of the coding sequence by providing the recognition for RNA polymerase and other factors required for proper transcription. For example, a promoter may contain a region containing basal promoter elements recognized by RNA polymerase, a region containing the 5' untranslated region (UTR) of a coding sequence, and optionally an intron. In some embodiments, a promoter comprises or consists of the about 2 kb region upstream (5') of the translation start site of a known or predicted coding sequence.

"Regulatory elements" and "regulatory sequences" are used interchangeably herein and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, terminators, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

A "terminator," as used herein, is responsible for the termination of transcription beyond the translation stop site of a coding sequence and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof).

Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used. For example, a terminator may contain a region containing the 3' untranslated region (UTR) of a coding sequence, and optionally additional 3' non-transcribed sequence. In some embodiments, a terminator comprises or consists of the about 1 kb region downstream (3') of the translation stop site of a known or predicted coding sequence.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Nontransformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as *Pseudomonas* HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene kn1, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the disclosure, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

The term "transformation" as used herein refers to the transfer of a nucleic acid into a host cell, preferably resulting in genetically stable integration, which includes integration into a chromosome and heritable extrachromosomal events. In some particular embodiments, the introduction into a plant, plant part and/or plant cell is via bacterial-mediated transformation, particle bombardment transformation (also called biolistic particle transformation), calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of a nucleic acid into the plant, plant part and/or cell thereof, or a combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A "transgenic plant" is a plant having one or more plant cells that contain a heterologous DNA sequence.

As used herein, "vector" includes reference to a nucleic acid used in transfection of a host cell and into which can be inserted a polynucleotide. Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

DETAILED DESCRIPTION

Aspects of the disclosure relate to regulatory elements, such as promoters and terminators, useful for expression of heterologous sequences in plants, such as soybean.

In some aspects, the disclosure provides a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-30, such as 1-5 or 8-29. In some embodiments, the nucleotide sequence comprises one or more of SEQ ID NOs: 1-30, such as 1-5 or 8-29. In some embodiments, the nucleotide sequence comprises one of SEQ ID Nos: 1-30, such as 1-5 and one of SEQ ID Nos: 8-29. In some embodiments, the disclosure provides a nucleotide sequence comprising a fragment, e.g., a biologically active fragment, of one or more of SEQ ID NOs: 1-30, such as 1-5 or 8-29 (e.g., a fragment of at least 100, at least 200, at least 300, at least 400, at least 500, at least 600, at least 700, at least 800, at least 900 or at least 1000 contiguous nucleotides of one or more of SEQ ID NOs: 1-30, such as 1-5 or 8-29). In some embodiments, the disclosure provides a nucleotide sequence comprising a fragment, e.g., a biologically active fragment, of one or more of SEQ ID NOs: 1-30, such as 1-5 or 8-29 (e.g., a fragment of at least 100, at least 200, at least 300, at least 400, at least 500, at least 600, at least 700, at least 800, at least 900 or at least 1000 contiguous nucleotides of one or more of SEQ ID NOs: 1-30, such as 1-5 or 8-29).

In some aspects, the disclosure provides an expression cassette. In some embodiments, the expression cassette comprises a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-30, such as 1-5 or 8-29, wherein the nucleotide sequence is operably linked to a heterologous nucleotide sequence. In some embodiments, the expression cassette comprises a nucleotide sequence comprising one or more of SEQ ID NOs: 1-30, such as 1-5 or 8-29. In some embodiments, the expression cassette comprises a nucleotide sequence comprising one of SEQ ID NOs: 1-30, such as 1-5 and one of 8-29. In some embodiments, the expression cassette comprises a nucleotide sequence comprising a fragment, e.g., a biologically active fragment, of one or more of SEQ ID NOs: 1-30, such as 1-5 or 8-29 (e.g., a fragment of at least 100, at least 200, at least 300, at least 400, at least 500, at least 600, at least 700, at least 800, at least 900 or at least 1000 contiguous nucleotides of one or more of SEQ ID NOs: 1-30, such as 1-5 or 8-29). In some embodiments, the expression cassette further comprises a selectable marker.

In some embodiments, the heterologous sequence is a nucleic acid of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process or altered reproductive capability. In some embodiments, the RNA or protein of interest comprises a genome editing agent, e.g., a CRISPR/Cas agent (such as a Cas protein and/or guide RNA), a TALEN, a DNA-guided nuclease, a meganuclease, a recombinase, or a zinc finger nuclease. In some embodiments, the heterologous nucleotide sequence encodes a selectable marker.

In some embodiments, the expression cassette is comprised within a vector, such as a plasmid, virus, or *Agrobacterium*. In some embodiments, the expression cassette is comprised within a plant cell. In some embodiments, the plant cell is a dicot cell. In some embodiments, the plant cell is a *Glycine max* cell. In some embodiments, the *Glycine max* cell is an elite *Glycine max* cell.

In some embodiments, the expression cassette is comprised within a transgenic plant. In some embodiments, the plant is a dicot. In some embodiments, the plant is a *Glycine max* plant. In some embodiments, the *Glycine max* plant is an elite *Glycine max* plant.

In some embodiments, the disclosure provides a seed from a transgenic plant, e.g., a seed comprising the expression cassette.

In some embodiments, the disclosure provides a commodity product produced from a transgenic plant or part thereof, e.g., a commodity product comprising the expression cassette. In some embodiments, the commodity product is selected from the group consisting of whole or processed seeds, flour, protein isolates, concentrates, liquids, syrups, pastes, sauces or other food or product.

Other aspects of the disclosure relate to a method, e.g., a transformation method, comprising introducing an expression cassette or vector as described herein into a plant or plant cell. In some embodiments, the introducing comprises *Agrobacterium*-mediated transformation. In some embodiments, the introducing comprises particle bombardment. In some embodiments of the method, the method further comprises placing the plant or plant cell under conditions whereby an RNA or protein of interest and/or a selectable marker is expressed from the expression cassette or vector. In some embodiments, the conditions are appropriate growth or maintenance conditions for the plant or plant cell. In some embodiments of the method, the method further comprises crossing the plant to a second plant to produce a progeny plant. In some embodiments of the method, the method further comprises self-crossing the plant to produce a progeny plant. In some embodiments, the plant or plant cell is a dicot plant or plant cell. In some embodiments, the plant or plant cell is a *Glycine max* plant or plant cell. In some embodiments, the plant or plant cell is an elite *Glycine max* plant or plant cell. In some embodiments, the second plant is an elite *Glycine max* plant.

Hereinafter, the present invention will be described in detail by the following examples. However, the following examples are illustrative of the present invention, and the scope of the present invention is not limited by the following examples.

EXAMPLES

Example 1: Identification and Characterization of Novel Promoter Sequences

Methods

Reference genomes from wild *Glycine* species (*Glycine argyrea*, *Glycine canescens*, *Glycine clandestine*, and *Glycine tomentella*) were used and candidate promoter sequences were obtained based on identification of orthologues to certain genes from *Glycine max*: Ubiquitin (Ubi), s-adenosyl methionine (SAM), actin depolymerizing factor (ADF3), and Translation elongation factor EF-1 alpha (EF1a). Additional candidate promoter sequences were identified using RNAseq data to identify genes in *Glycine max* with expression between 12-18 log 2 normalized data and putative promoter sequences from those genes were added as candidates. The candidate promoter sequences were the 2 kb region upstream of the predicted or known translation start site. The candidate promoter sequences were expected to contain the basal promoter elements, as well as the 5' UTR and potentially an intron (depending on the structure of the predicted or known coding sequence).

Vectors were designed for each candidate promoter, each of which contained a soy codon-optimized Bx9, a maize UDP-Glucosyl transferase, benzoxazinoid 9 (see International Publication No. WO2018213022 for description of maize Bx9), as a reporter gene and the terminator sequence tMt51186 (SEQ ID NO: 30). For cloning convenience, mutations were made in the promoter sequence to remove any NcoI and SacI sites. The ATGs in the 5' UTR were also mutated.

Vectors were first screened by transient transformation. All vectors were compared to average expression levels of a vector containing a baseline positive control promoter (prGmSAMS, SEQ ID NO: 7). Transient transformation was performed using 14 day old soy plants. The first trifoliate set of leaves were damaged on the abaxial side using a wire brush. The plant leaves were then immersed in an *Agrobacterium* solution containing the test construct in addition to an internal control construct at a 1:1 ratio. Each *Agrobacterium* was adjusted to OD=1.0 at 600 nm. The immersed plants were placed in a vacuum chamber and vacuum was applied for 3-5 minutes. The infiltrated plants were placed in a tray with a clear plastic lid to maintain the humidity. The infiltrated leaves were sampled in 96 well block for ELISA assay 4 days after infiltration. The ELISA employed two polyclonal antibodies which have been produced against the BX9 protein. High-binding polystyrene plates (Nunc Maxisorp #430341) were coated at 4 C overnight with 10 ug/ml goat anti-BX9 in 25 mM borate, 75 mM NaCl, pH 8.5. Plates were washed five times with Phosphate Buffered Saline +0.05% Tween-20 (PBST). Standards (160, 80, 40, 20, 10, 5, 2.5, and 0 ng/ml of purified BX9 protein) were prepared in ELISA diluent (PB ST+1% bovine serum albumin) One hundred microliters of each appropriately diluted sample or standard was added to the plate, incubated for 1 hr at ambient temperature with shaking at 200 rpm, and washed five times. Rabbit anti-BX9 (100 ul/well) diluted to 1 ug/ml in ELISA diluent was then added to the plate, incubated for 1 hr at ambient temperature with shaking at 200 rpm, and washed as before. Donkey anti-rabbit conjugated to alkaline phosphatase (Jackson ImmunoResearch, West Grove, PA) at 1 ug/ml in ELISA diluent was added to the plate (100 ul/well), incubated at ambient temperature with shaking at 200 rpm, and washed. Substrate p-nitrophenyl phosphate (Surmodics, Eden Prairie, MN) was added and allowed to develop for 15-30 mM at ambient temperature. The absorbance was measured at 405 nm using a microplate reader (BioTek Powerwave XS2, Winooski, VT). The standard curve used a four-parameter curve fit to plot the concentrations versus the absorbance. To normalize for extraction efficiency, the concentration of the analyte (BX9) was divided by the concentration of the total soluble protein (TSP). TSP was measured using the Pierce™ BCA (bicinchoninic acid) protein assay (ThermoFisher Scientific).

Based on the data generated, a vector containing prGaSAMS599400 (see Table 1) was selected as a negative control for additional studies.

A subset of the vectors were then selected and stably transformed into soybean plants and were validated at T0 and T1 events and compared to the positive control and negative control. Soybean (*Glycine max*, variety 06KG212440) seeds were sterilized with chlorine gas overnight. Sterilized seeds were imbibed in germination media (SoyGerm) with the hilum side facing down. The seeds were incubated at 22-24° C. in the dark for about 16 hours. Imbibed seeds were used to prepare explants as described in International Publication No. WO2004000006. The prepared explants were immediately infected with a disarmed Chry5d3 *Agrobacterium tumafaciens* strain containing respective binary vector by mixing the isolated immature seed explants with bacterial suspension in infection medium (SoyInf: ½×MS salts, 1×B5 vitamins, 2 g/L sucrose, 1 g/L glucose, 4 g/L MES [2-(Nmorpholino) ethanesulfonic acid], 2 mg/L zeatin riboside and 200 μM acetosyringone, pH 5.4). The mixture was incubated for at least 30 minutes or up to overnight at room temperature. Following infection, the explants were removed from the *Agrobacterium* suspension and placed on a co-cultivation medium such as SoyCCM 2Zt (½×MS salts, 1×B5 vitamins, 2 g/L sucrose, 1 g/L glucose, 4 g/L MES, 2 mg/L zeatin riboside and 200 µM acetosyringone, pH 5.4, with 6 g/L purified agar), preferably adaxial (flat) side up. The co-cultivation plates were incubated for 3 to 5 days at 23° C. in the dark.

After co-cultivation, elongated hypocotyls of the explants were trimmed back just below the cotyledon nodes. The explants were transferred to recovery medium without selection agent such as SoyR0 (3.1 g/L B5 salts, 1×B5 vitamins, 0.8×MS Iron, 3% sucrose, 1 g/L MES, 2 mg/L BAP, 0.1 g/L Asparagine, 50 mg/L timentin, 200 mg 1-1 cefotaxime and 50 mg/L vancomycin, 7 g/L agar, pH 5.7) with appropriate antibiotics to inhibit *Agrobacterium* growth. The cotyledon node end was inserted into the media. The plates with the explants were incubated for about 7-10 days at 24 degrees C. under 16 hours light/8 hours dark regimen, and >80 µE/m2/s.

After the recovery period, the explants were transferred to regeneration media such as SoyR1 (3.1 g/L B5 salts, 1×B5 vitamins, 0.8×MS Iron, 3% sucrose, 1 g/L MES, 2 mg/L BAP, 0.1 g/L Asparagine, 7 g/L purified agar, pH 5.7, along with appropriate selection agent, e.g. ALS herbicide or glyphosate) along with the cotyledon for about 2-3 weeks.

After about 2-3 weeks in regeneration/selection media such as SoyR1, developing multiple shoots clusters were transferred to elongation medium SoyE1 (1×MS basal salts, 1×B5 vitamins, 0.8×MS iron, 3% sucrose, 0.6 g/L MES, 50 mg/L asparagine, 100 mg/L glutamic acid, 0.1 mg/L IAA, 0.5 mg/L GA3, 1 mg/L zeatin riboside, 50 mg/L Ticarcillin, 75 mg/L cefotaxime, pH 5.7, solidified with 0.7% agar along with appropriate selection agent, e.g. ALS herbicide or glyphosate) for shoot elongation. Subcultures to fresh elongation media SoyE1 were performed every 2-4 weeks until elongated shoots (>3 cm) were long enough to be transferred into soil for direct rooting in a tray inside a hole-less secondary tray filled with water to keep the soil wet. The plastic dome was removed after about 2 weeks and leaves were sampled for Taqman analysis to identify plants positive for gene-of-interest.

Results 31 vectors containing 31 different candidate promoters were tested in a transient transformation assay. Of those 31, five were found to have expression levels comparable to or better than a positive control promoter known to have high constitutive expression (see Table 1). A promoter having poor expression relative to the control in the assay, prGaSAMS599400, was selected to be used as a negative control in the stable transformation assay.

TABLE 1

Promotor transient transformation expression assay results

| Promoter name | Promoter SEQ ID NO | # Replicates (n) | % Expression of Baseline Control | Coefficient of variation (% CV) Replicates |
|---|---|---|---|---|
| prGaUbiPI599400 | 1 | 10 | 287% | 15% |
| prGcUbiPI339656 | 2 | 5 | 237% | 28% |
| prGtUbiPI505267 | 3 | 13 | 164% | 40% |
| prGaEF1aPI599400 | 4 | 10 | 104% | 42% |
| prGmEF1aGlyma17G186600 | 5 | 15 | 74% | 27% |
| prGaSAMS599400 | 6 | 8 | 12% | 23% |
| prGmSAMS (control) | 7 | 16 | 100% | 52% |

Four of the candidate promoters shown to have better activity in Table 1 compared to the positive control were then assayed in a stable transformation assay.

The four candidate promoters were shown to drive higher Bx9 expression in seedling leaf than the positive control in both transient and TO events (see Table 2, TO data are from single copy events).

TABLE 2

Expression of reporter in seedling leaf

| | | Transient ELISA | |
|---|---|---|---|
| Construct | Cassette | n | % to control |
| 24244 | prGaUbiPI599400, Bx9, tMt51186 | 10 | 287 |
| 24245 | prGcUbiPI339656, Bx9, tMt51186 | 5 | 237 |
| 24246 | prGtUbiPI505267, Bx9, tMt51186 | 13 | 164 |
| 24247 | prGaEF1aPI599400, Bx9, tMt51186 | 16 | 104 |
| 24249 (negative control) | prGaSAMSPI599400, Bx9, tMt51186 | 8 | 12 |
| 24276 (positive control) | prGmSAMS, Bx9, tMt51186 | 27 | 100 |

TABLE 2-continued

Expression of reporter in seedling leaf

| Construct | Cassette (promoter, coding sequence, terminator) | n | Stable transformant ELISA avg (ng/mg TSP) | % to control |
|---|---|---|---|---|
| 24244 | prGaUbiPI599400, Bx9, tMt51186 | 8 | 95 | 188 |
| 24245 | prGcUbiPI339656, Bx9, tMt51186 | 8 | 81 | 161 |
| 24246 | prGtUbiPI505267, Bx9, tMt51186 | 13 | 75 | 149 |
| 24247 | prGaEF1aPI599400, Bx9, tMt51186 | 13 | 83 | 164 |
| 24249 (negative control) | prGaSAMSPI599400, Bx9, tMt51186 | 15 | 17 | 34 |
| 24276 (positive control) | prGmSAMS, Bx9, tMt51186 | 14 | 50 | 100 |

| Construct (promoter) | Cassette | T0 events Average (ng/mg TSP) | T0 events % to prGmUbi control | T1 events Average (ng/mg TSP) | T1 events % to prGmUbi control |
|---|---|---|---|---|---|
| 24705 (prGaUbiPI599400-02) | prGaUbiPI599400-02, cCP4EPSPSCTP2-01, tPsE9-01 | 773 | 71 | 1269 | 70 |
| 23830 (prGmUbi1-02, positive control) | prGmUbi1-02, cCP4EPSPSCTP2-01, tPsE9-01 | 1092 | 100 | 1809 | 100 |

Figure 1:
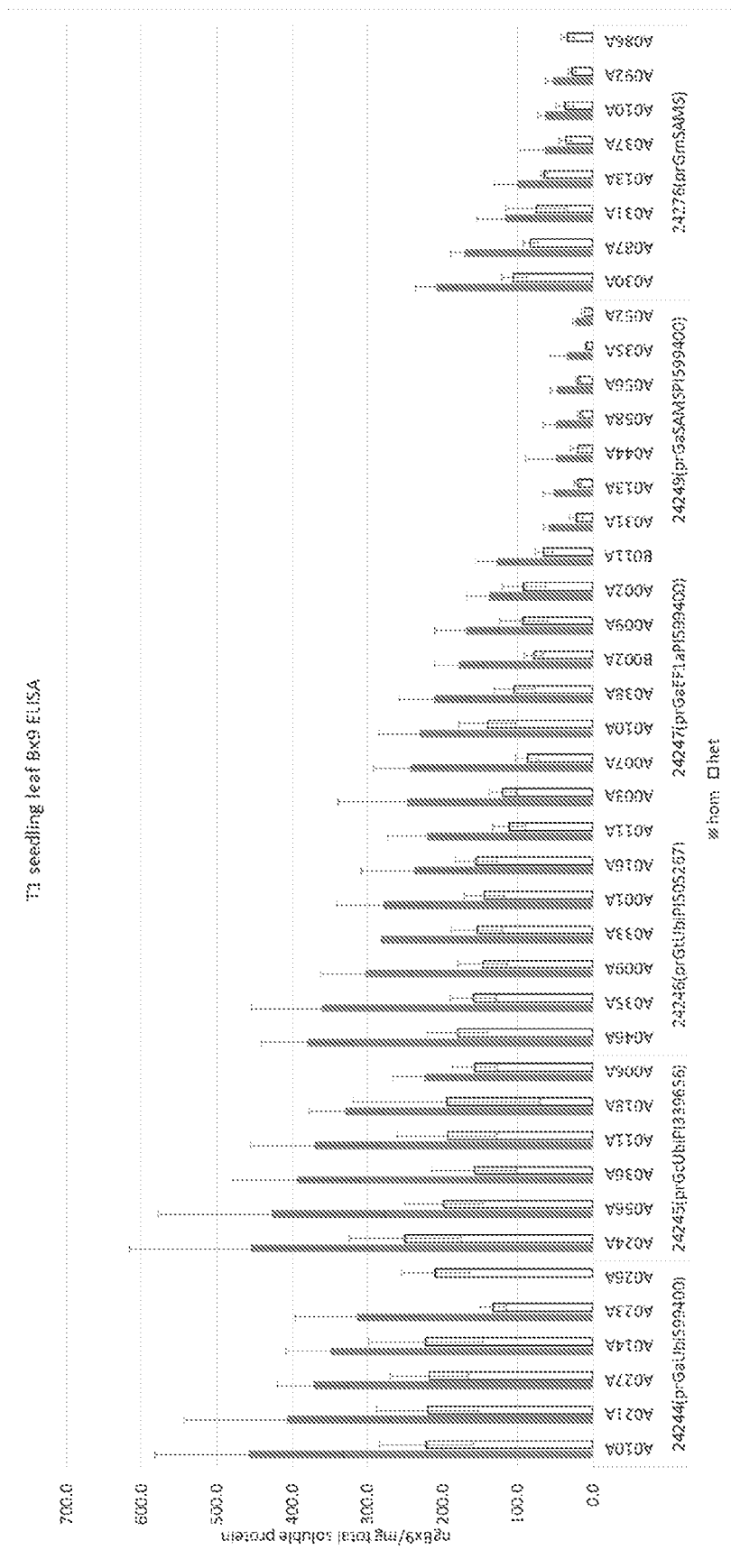
FIG. 1 is a graph showing Bx9 expression in T1 soybean seedling leaf. Hom=homozygous, Het=heterozygous. 24244=prGaUbi599400; 24245=prGcUbiPI339656; 24246=prGtUbiPI505267; 24247=prGaEF1aPI599400; 24249=prGaSAMSPI599400, negative control.

The four candidate promoters were also shown to drive higher Bx9 expression in T1 seedling leaf compared to the positive control (see FIG. 1). The four candidate promoters were also shown to drive higher Bx9 expression in T1 mature leaf and T1 root at reproductive stage compared to the positive control (see FIGS. 2 and 3). The four candidate promoters were also shown to drive higher or comparable Bx9 expression in T1 seed pod compared to the positive control (see FIG. 4). Three of the four candidate promoters were also shown to drive higher or comparable Bx9 expression in T1 embryo compared to the positive control (see FIG. 5). Promoter prGaUbiPI599400 was modified to create prGaUbiPI599400-02 which drove expression of cCP4EPSPSCTP2-01 at acceptable levels. Additional data showing the comparison between the promoters at different stages is shown below in Table 3.

TABLE 3

Promoter comparison at the construct level

| Construct (promoter) | N | Vegetative stage Seedling leaf Average (ng/mg TSP) | Vegetative stage Seedling leaf % to prSAMS control | Reproductive stage Mature leaf Average (ng/mg TSP) | Reproductive stage Mature leaf % to prSAMS control |
|---|---|---|---|---|---|
| 24244 (prGaUbi599400) | 15 | 369 | 333 | 135 | 656 |
| 24245 (prGcUbiPI339656) | 18 | 364 | 329 | 123 | 597 |
| 24246 (prGtUbiPI505267) | 18 | 291 | 262 | 88 | 426 |
| 24247 (prGaEF1aPI599400) | 24 | 183 | 165 | 48 | 234 |
| 24249 (prGaSAMSPI599400, negative control) | 21 | 42 | 38 | 13 | 62 |
| 24276 (prGmSAMS, positive control) | 21 | 111 | 100 | 21 | 100 |

TABLE 3-continued

Promoter comparison at the construct level

| | | Reproductive stage | | | | | |
|---|---|---|---|---|---|---|---|
| | | Root | | Seed pod shell | | Embryo | |
| Construct (promoter) | N | Average (ng/mg TSP) | % to prSAMS control | Average (ng/mg TSP) | % to prSAMS control | Average (ng/mg TSP) | % to prSAMS control |
| 24244 (prGaUbi599400) | 15 | 1202 | 1251 | 1268 | 243 | 4211 | 207 |
| 24245 (prGcUbiPI339656) | 18 | 468 | 488 | 1210 | 232 | 454 | 22 |
| 24246 (prGtUbiPI505267) | 18 | 338 | 352 | 1425 | 273 | 1535 | 75 |
| 24247 (prGaEF1aPI599400) | 24 | 212 | 221 | 586 | 112 | 641 | 31 |
| 24249 (prGaSAMSPI599400, negative control) | 21 | 11 | 12 | 53 | 10 | 64 | 3 |
| 24276 (prGmSAMS, positive control) | 21 | 96 | 100 | 522 | 100 | 2039 | 100 |

Taken together, these data show that the four selected candidate promoters are highly expressed in multiple tissues and are expected to be useful as constitutive promoters for use in expression constructs in soybean.

Example 2: Identification and Characterization of Novel Terminator Sequences Methods Candidate terminator sequences were derived from the genes tested in Example 1 and tested for terminator activity. The candidate terminator sequences were the 1 kb region downstream of the predicted or known translation stop site. The candidate terminator sequences were expected to contain the 3' UTR and potentially additional 3' non-transcribed sequence (depending on the structure of the predicted or known coding sequence).

Vectors were designed for each candidate terminator, each of which contained Bx9 as a reporter gene and the promoter sequence prGmSAMS (SEQ ID NO: 7). Vectors were first screened by transient transformation using the methods describe in Example 1. All vectors were compared to average expression levels of a vector containing a baseline positive control terminator (tMt51186, SEQ ID NO: 30). Expression levels were measured by ELISA as described in Example 1.

A subset of the vectors were then selected and stably transformed into soybean plants and were validated at T0 and T1 events and compared to the positive control and negative control. The transformation and analysis methods are the same as those described in Example 1.

Results 29 vectors containing 29 different candidate terminators were tested in a transient transformation assay. Of those 29, 22 were found to have expression levels comparable to or better than a positive control terminator known to support high constitutive expression (see Table 4).

TABLE 4

Terminator transient transformation expression assay results

| Terminator Name | Terminator SEQ ID NO | % Baseline Ctl | # Replicates | % CV |
|---|---|---|---|---|
| tGmEF1a17G18600 | 8 | 370% | 8 | 35% |
| tGtUbiPI505267 | 9 | 339% | 8 | 57% |
| tGaEF1aPI599400 | 10 | 311% | 8 | 11% |
| tGmMIP02G255000 | 11 | 272% | 8 | 18% |
| tGtMIPPI505267 | 12 | 216% | 7 | 13% |
| tGlMIPPI546970 | 13 | 214% | 8 | 24% |
| tGcUbiPI339656 | 14 | 210% | 8 | 27% |
| tGtEF1aPI441001 | 15 | 204% | 8 | 32% |
| tGaUbiPI599400 | 16 | 196% | 8 | 54% |
| tGcUbiPI595799 | 17 | 185% | 8 | 31% |
| tGcSAMSPI339656 | 18 | 148% | 8 | 26% |
| tGmRBPGlyma11G117300 | 19 | 144% | 8 | 35% |
| tGmMIPGlyma19G186100 | 20 | 133% | 8 | 24% |
| tGaSAMSPI599400 | 21 | 120% | 8 | 43% |
| tGaMIPPI505151 | 22 | 118% | 5 | 63% |
| tGtEF-02PI441001 | 23 | 114% | 8 | 32% |
| tGaEF-02PI599400 | 24 | 110% | 8 | 60% |
| tGaADF3PI599400 | 25 | 105% | 8 | 13% |
| tGcEF-02PI483193 | 26 | 103% | 8 | 32% |

TABLE 4-continued

Terminator transient transformation expression assay results

| Terminator Name | Terminator SEQ ID NO | % Baseline Ctl | # Replicates | % CV |
|---|---|---|---|---|
| tGmPOGXGlyma07G260300 | 27 | 97% | 8 | 12% |
| tGtSAMsPI505267 | 28 | 96% | 8 | 29% |
| tGaRBPPI599400 | 29 | 86% | 8 | 25% |
| Baseline Control (tMt51186) | 30 | 100% | 28 | 57% |

Six of the candidate terminators shown to have better activity in Table 4 compared to the positive control were then assayed in a stable transformation assay.

The six candidate terminators were shown to drive higher Bx9 expression in seedling leaf than the positive control in both transient and TO events (see Table 5, TO data are from single copy events).

TABLE 5

Expression of reporter in seedling leaf

| Construct | Cassette (promoter, coding sequence, terminator) | Transient ELISA n | % to control | Stable Transformant ELISA avg n | (ng/mg TSP) | % to control |
|---|---|---|---|---|---|---|
| 24321 | prGmSAMS, Bx9, tGmEF1a17G18600 | 8 | 370 | 12 | 175 | 282 |
| 24322 | prGmSAMS Bx9, tGaEF1aPI599400 | 8 | 339 | 7 | 192 | 310 |
| 24323 | prGmSAMS, Bx9, tGtUbiPI505267 | 8 | 311 | 9 | 131 | 211 |
| 24324 | prGmSAMS, Bx9, tGcUbiPI339656 | 8 | 272 | 6 | 156 | 252 |
| 24325 | prGmSAMS, Bx9, tGmMIP02G255000 | 8 | 214 | 9 | 113 | 182 |
| 24326 | prGmSAMS, Bx9, tGlMIPPI546970 | 8 | 210 | 8 | 160 | 258 |
| 24327 (positive control) | prGmSAMS, Bx9, tMt51186 | 8 | 100 | 8 | 62 | 100 |

The six candidate terminators were also shown to drive higher or comparable Bx9 expression in T1 seedling leaf compared to the positive control (see FIG. 6). The six candidate terminators were also shown to drive higher or comparable Bx9 expression in T1 mature leaf and T1 root at reproductive stage compared to the positive control (see FIGS. 7 and 8). The six candidate terminators were also shown to drive higher or comparable Bx9 expression in T1 seed pod compared to the positive control (see FIG. 9). Five of the six candidate terminators were also shown to drive higher or comparable Bx9 expression in T1 embryo compared to the positive control (see FIG. 10). Additional data showing the comparison between the promoters at different stages is shown below in Table 6.

TABLE 6

Terminator comparison at the construct level

| Construct (terminator) | N | Vegetative stage Seedling Leaf Average (ng/mg TSP) | % to tMt51186 control | Reproductive stage Mature Leaf Average (ng/mg TSP) | % to tMt51186 control |
|---|---|---|---|---|---|
| 24321 (tGmEF1a17G18600) | 18 | 372 | 280 | 446 | 233 |
| 24322 (tGaEF1aPI599400) | 12 | 491 | 369 | 536 | 279 |
| 24323 (tGtUbiPI505267) | 18 | 209 | 157 | 448 | 234 |
| 24324 (tGcUbiPI339656) | 17 | 149 | 112 | 243 | 127 |
| 24325 (tGmMIP02G255000) | 15 | 225 | 169 | 309 | 161 |
| 24326 (tGlMIPPI546970) | 15 | 230 | 173 | 485 | 253 |
| 24327 (tMt51186, control) | 15 | 133 | 100 | 192 | 100 |

TABLE 6-continued

Terminator comparison at the construct level

| | | Reproductive stage | | | | | |
| --- | --- | --- | --- | --- | --- | --- | --- |
| | | Root | | Seed Pod | | Embryo | |
| Construct (terminator) | N | Average (ng/mg TSP) | % to tMt51186 control | Average (ng/mg TSP) | % to tMt51186 control | Average (ng/mg TSP) | % to tMt51186 control |
| 24321 (tGmEF1a17G18600) | 18 | 875 | 184 | 1666 | 315 | 697 | 170 |
| 24322 (tGaEF1aPI599400) | 12 | 1033 | 218 | 2343 | 443 | 616 | 150 |
| 24323 (tGtUbiPI505267) | 18 | 810 | 171 | 1588 | 300 | 463 | 113 |
| 24324 (tGcUbiPI339656) | 17 | 558 | 118 | 977 | 185 | 462 | 112 |
| 24325 (tGmMIP02G255000) | 15 | 491 | 103 | 885 | 167 | 228 | 56 |
| 24326 (tGlMIPPI546970) | 15 | 473 | 100 | 838 | 158 | 546 | 133 |
| 24327 (tMt51186, control) | 15 | 475 | 100 | 529 | 100 | 411 | 100 |

Note: Average is Bx9 expression (ng Bx9/mg total soluble protein) in homozygous T1 plants Taken together, these data show that the six selected candidate terminators support high expression in multiple tissues and are expected to be useful in expression constructs in soybean.

What is claimed is:

1. An expression cassette comprising a nucleotide sequence with one or more of SEQ ID NO: 1, wherein the nucleotide sequence is operably linked to a heterologous nucleotide sequence.

2. An expression cassette comprising a first nucleotide sequence with one or more of SEQ ID NO: 1 and a second nucleotide sequence with one or more of SEQ ID NO: 10, wherein the first and/or second nucleotide sequence are operably linked to a heterologous nucleotide sequence.

3. The expression cassette of claim 1, wherein the heterologous nucleotide sequence is a nucleic acid of interest that encodes an RNA or protein of interest.

4. The expression cassette of claim 3, wherein the RNA or protein of interest is capable of conferring upon a plant a desired characteristic selected from the group consisting of antibiotic resistance, virus resistance, insect resistance, disease resistance, resistance to other pests, herbicide tolerance, improved nutritional value, improved performance in an industrial process and altered reproductive capability.

5. The expression cassette of claim 1, wherein the heterologous nucleotide sequence encodes a selectable marker or wherein the expression cassette further comprises a selectable marker.

6. A vector comprising the expression cassette of claim 1.

7. The vector of claim 6, wherein the vector is a plasmid, virus, or *Agrobacterium*.

8. A plant cell comprising the expression cassette of vector of claim 1.

9. The plant cell of claim 8, wherein the plant cell is a dicot cell.

10. The plant cell of claim 9, wherein the plant cell is a *Glycine* max cell.

11. A transgenic plant comprising the plant cell of claim 8.

12. The transgenic plant of claim 11, wherein the plant is a dicot.

13. The transgenic plant of claim 12, wherein the plant is a *Glycine* max plant.

14. A seed from the transgenic plant of claim 1.

15. A method, comprising introducing the expression cassette of claim 1 into a plant or plant cell.

16. The method of claim 15, further comprising placing the plant or plant cell under conditions whereby an RNA or protein of interest and/or a selectable marker is expressed from the expression cassette or vector.

17. The method of claim 15, further comprising crossing the plant to a second plant or self-crossing the plant to produce a progeny plant.

18. A transgenic plant produced by the method of claim 15, or a plant part thereof wherein the plant part comprises the expression cassette.

19. The transgenic plant, or part thereof, of claim 18, wherein the plant is a dicot, optionally wherein the plant is a *Glycine* max plant.

* * * * *